United States Patent
Ziebol et al.

(10) Patent No.: US 11,944,776 B2
(45) Date of Patent: Apr. 2, 2024

(54) PERITONEAL DIALYSIS CAPS, SYSTEMS AND METHODS

(71) Applicant: ICU Medical, Inc., San Clemente, CA (US)

(72) Inventors: Robert J. Ziebol, Shoreview, MN (US); Matthew David Beilke, Plymouth, MN (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 18/320,769

(22) Filed: May 19, 2023

(65) Prior Publication Data

US 2023/0285735 A1    Sep. 14, 2023

Related U.S. Application Data

(63) Continuation of application No. PCT/US2021/062079, filed on Dec. 6, 2021.

(60) Provisional application No. 63/122,470, filed on Dec. 7, 2020.

(51) Int. Cl.
*A61M 39/20* (2006.01)
*A61M 39/16* (2006.01)

(52) U.S. Cl.
CPC .......... *A61M 39/20* (2013.01); *A61M 39/162* (2013.01); *A61M 39/165* (2013.01)

(58) Field of Classification Search
CPC ... A61M 39/20; A61M 39/162; A61M 39/165
See application file for complete search history.

(56) References Cited

U.S. PATENT DOCUMENTS

| | | |
|---|---|---|
| 382,297 A | 5/1888 | Fry |
| 559,697 A | 5/1896 | Tiugti et al. |
| 877,946 A | 2/1908 | Overton |

(Continued)

FOREIGN PATENT DOCUMENTS

| | | |
|---|---|---|
| CA | 2 148 847 | 12/1995 |
| CA | 2825217 | 3/2007 |

(Continued)

OTHER PUBLICATIONS

Antibiotic Lock Therapy Guideline, Stanford Hospital and Clinics, Pharmacy Department Policies and Procedures, issued Jun. 2011.

(Continued)

*Primary Examiner* — Ariana Zimbouski
*Assistant Examiner* — John A Doubrava
(74) *Attorney, Agent, or Firm* — Knobbe Martens Olson & Bear LLP

(57) ABSTRACT

A cap for a medical connector, the cap including a body having a closed proximal end and an open distal end, an interior volume within the body, an elongate member comprising an antimicrobial extending from the proximal end of body axially through at least a portion of the interior volume, the elongate member, threads for securing the cap to a medical connector, and a radially inwardly facing sealing surface on the cap, the inwardly facing sealing surface located distal to the threads and providing a liquid-tight seal between the cap and the medical connector when the cap is installed on the medical connector.

25 Claims, 18 Drawing Sheets

(56) References Cited

U.S. PATENT DOCUMENTS

| | | |
|---|---|---|
| 975,939 A | 11/1910 | Edwards et al. |
| 1,445,642 A | 2/1923 | O'Neill |
| 1,793,068 A | 2/1931 | Dickinson |
| 2,098,340 A | 11/1937 | Henahan |
| 2,436,297 A | 2/1948 | Guarnaschelli |
| 2,457,052 A | 12/1948 | Le Clair |
| 2,771,644 A | 11/1956 | Martin |
| 2,842,382 A | 7/1958 | Franck |
| 2,968,497 A | 1/1961 | Treleman |
| 3,127,892 A | 4/1964 | Bellamy, Jr. et al. |
| 3,262,448 A | 7/1966 | Ring et al. |
| 3,270,743 A | 9/1966 | Gingras |
| 3,301,392 A | 1/1967 | Eddingfield |
| 3,304,047 A | 2/1967 | Martin |
| 3,334,860 A | 8/1967 | Bolton, Jr. |
| 3,411,665 A | 11/1968 | Blum |
| 3,484,121 A | 12/1969 | Quinton |
| 3,485,416 A | 12/1969 | Fohrman |
| 3,538,950 A | 11/1970 | Porteners |
| 3,595,241 A | 7/1971 | Sheridan |
| 3,604,582 A | 9/1971 | Boudin |
| 3,707,972 A | 1/1973 | Villari et al. |
| 3,729,031 A | 4/1973 | Baldwin |
| 3,882,858 A | 5/1975 | Klemm |
| 3,977,401 A | 8/1976 | Pike |
| 3,977,517 A | 8/1976 | Kadlecik et al. |
| 3,987,930 A | 10/1976 | Fuson |
| 3,993,066 A | 11/1976 | Virag |
| 4,041,934 A | 8/1977 | Genese |
| 4,046,889 A | 9/1977 | Ondetti et al. |
| 4,052,511 A | 10/1977 | Cushman et al. |
| 4,053,052 A | 10/1977 | Jasper |
| 4,053,651 A | 10/1977 | Ondetti et al. |
| 4,066,067 A | 1/1978 | Micheli |
| 4,076,285 A | 2/1978 | Martinez |
| 4,078,686 A | 3/1978 | Karesh et al. |
| 4,079,738 A | 3/1978 | Dunn et al. |
| 4,095,810 A | 6/1978 | Kulle |
| 4,113,751 A | 9/1978 | Arnold |
| 4,121,585 A | 10/1978 | Becker, Jr. |
| 4,129,571 A | 12/1978 | Ondetti et al. |
| 4,133,441 A | 1/1979 | Mittleman et al. |
| 4,143,853 A | 3/1979 | Abramson |
| 4,150,845 A | 4/1979 | Kopacz et al. |
| 4,154,840 A | 5/1979 | Ondetti et al. |
| 4,154,960 A | 5/1979 | Ondetti et al. |
| 4,192,443 A | 3/1980 | McLaren |
| 4,194,509 A | 3/1980 | Pickering et al. |
| 4,195,632 A | 4/1980 | Parker et al. |
| 4,233,982 A | 11/1980 | Bauer et al. |
| 4,243,035 A | 1/1981 | Barrett |
| 4,245,635 A | 1/1981 | Kontos |
| 4,264,664 A | 4/1981 | Kunz |
| 4,280,632 A | 7/1981 | Yuhara |
| 4,294,370 A | 10/1981 | Toeppen |
| 4,317,446 A | 3/1982 | Ambrosio et al. |
| 4,324,239 A | 4/1982 | Gordon et al. |
| 4,325,368 A | 4/1982 | Kaemmerer |
| 4,331,783 A | 5/1982 | Stoy |
| 4,334,551 A | 6/1982 | Pfister |
| 4,335,756 A | 6/1982 | Sharp et al. |
| 4,337,327 A | 6/1982 | Stoy |
| 4,340,049 A | 7/1982 | Munsch |
| 4,340,052 A | 7/1982 | Dennehey et al. |
| 4,354,490 A | 10/1982 | Rogers |
| 4,369,294 A | 1/1983 | Stoy |
| 4,370,451 A | 1/1983 | Stoy |
| 4,379,458 A | 4/1983 | Bauer et al. |
| 4,379,874 A | 4/1983 | Stoy |
| 4,384,589 A | 5/1983 | Morris |
| 4,387,879 A | 6/1983 | Tauschinski |
| 4,390,016 A | 6/1983 | Riess |
| 4,397,442 A | 8/1983 | Larkin |
| 4,402,691 A | 9/1983 | Rosenthal et al. |
| 4,405,312 A | 9/1983 | Gross et al. |
| 4,417,890 A | 11/1983 | Dennehey et al. |
| 4,420,589 A | 12/1983 | Stoy |
| 4,427,126 A | 1/1984 | Ostrowsky |
| 4,430,073 A | 2/1984 | Bemis et al. |
| 4,432,764 A | 2/1984 | Lopez |
| 4,432,766 A | 2/1984 | Bellotti et al. |
| 4,436,125 A | 3/1984 | Blenkush |
| 4,439,179 A | 3/1984 | Lueders et al. |
| 4,439,184 A | 3/1984 | Wheeler |
| 4,440,207 A | 4/1984 | Genatempo et al. |
| 4,444,310 A | 4/1984 | Odell |
| 4,446,967 A | 5/1984 | Halkyard |
| 4,447,419 A | 5/1984 | Quadro |
| 4,457,749 A | 7/1984 | Bellotti et al. |
| 4,461,368 A | 7/1984 | Plourde |
| 4,461,896 A | 7/1984 | Portlock |
| 4,480,940 A | 11/1984 | Woodruff |
| 4,507,111 A | 3/1985 | Gordon et al. |
| 4,511,359 A | 4/1985 | Vaillancourt |
| 4,534,764 A | 8/1985 | Mittleman et al. |
| 4,538,836 A | 9/1985 | Kruetten |
| 4,559,043 A | 12/1985 | Whitehouse |
| 4,568,675 A | 2/1986 | Bush et al. |
| 4,585,758 A | 4/1986 | Huang et al. |
| 4,602,042 A | 7/1986 | Chantler et al. |
| 4,610,469 A | 9/1986 | Wolff-Mooij |
| 4,619,640 A | 10/1986 | Potolsky et al. |
| 4,623,332 A | 11/1986 | Lindmayer et al. |
| 4,624,664 A | 11/1986 | Peluso et al. |
| 4,626,545 A | 12/1986 | Taub |
| 4,629,159 A | 12/1986 | Wellenstam |
| 4,631,188 A | 12/1986 | Stoy |
| 4,642,091 A | 2/1987 | Richmond |
| 4,660,803 A | 4/1987 | Johnston et al. |
| 4,662,878 A | 5/1987 | Lindmayer |
| 4,666,057 A | 5/1987 | Come et al. |
| 4,666,427 A | 5/1987 | Larsson et al. |
| 4,671,306 A | 6/1987 | Spector |
| 4,671,412 A | 6/1987 | Gatten |
| 4,681,886 A | 7/1987 | Haugwitz et al. |
| 4,692,458 A | 9/1987 | Ryan et al. |
| 4,692,459 A | 9/1987 | Ryan et al. |
| 4,700,744 A | 10/1987 | Rutter et al. |
| 4,703,762 A | 11/1987 | Rathbone et al. |
| 4,705,790 A | 11/1987 | Hubele et al. |
| 4,723,603 A | 2/1988 | Plummer |
| 4,728,075 A | 3/1988 | Paradis |
| 4,728,321 A | 3/1988 | Chen |
| 4,738,668 A | 4/1988 | Bellotti et al. |
| 4,745,950 A | 5/1988 | Mathieu |
| 4,747,502 A | 5/1988 | Luenser |
| 4,748,160 A | 5/1988 | Bennion et al. |
| 4,752,983 A | 6/1988 | Grieshaber |
| 4,769,013 A | 9/1988 | Lorenz et al. |
| 4,774,964 A | 10/1988 | Bonaldo |
| 4,774,965 A | 10/1988 | Rodriguez et al. |
| 4,778,447 A | 10/1988 | Velde et al. |
| 4,781,702 A | 11/1988 | Herrli |
| 4,799,926 A | 1/1989 | Haber |
| 4,804,015 A | 2/1989 | Albinsson |
| 4,808,158 A | 2/1989 | Kreuzer et al. |
| 4,810,241 A | 3/1989 | Rogers |
| 4,811,847 A | 3/1989 | Reif et al. |
| 4,813,933 A | 3/1989 | Turner |
| 4,816,024 A | 3/1989 | Sitar et al. |
| 4,834,271 A | 5/1989 | Litwin |
| 4,862,913 A | 9/1989 | Wildfang |
| 4,874,366 A | 10/1989 | Zdeb et al. |
| 4,883,483 A | 11/1989 | Lindmayer |
| 4,889,255 A | 12/1989 | Schiemann et al. |
| 4,894,056 A | 1/1990 | Bommarito |
| 4,898,580 A | 2/1990 | Crowley |
| 4,915,687 A | 4/1990 | Sivert |
| 4,917,669 A | 4/1990 | Bonaldo |
| 4,919,658 A | 4/1990 | Badia |
| 4,927,019 A | 5/1990 | Haber et al. |
| 4,935,010 A | 6/1990 | Cox et al. |
| 4,941,873 A | 7/1990 | Fischer |
| 4,950,260 A | 8/1990 | Bonaldo |

(56) References Cited

U.S. PATENT DOCUMENTS

| | | |
|---|---|---|
| 4,957,637 A | 9/1990 | Cornell |
| 4,963,132 A | 10/1990 | Gibson |
| D313,277 S | 12/1990 | Haining |
| D314,050 S | 1/1991 | Sone |
| 4,983,161 A | 1/1991 | Dadson et al. |
| 4,985,017 A | 1/1991 | Theeuwes |
| 4,989,733 A | 2/1991 | Patry |
| 4,991,629 A | 2/1991 | Ernesto et al. |
| 4,997,371 A | 3/1991 | Fischer |
| 4,999,210 A | 3/1991 | Solomon et al. |
| 5,002,964 A | 3/1991 | Loscalzo |
| 5,006,114 A | 4/1991 | Rogers et al. |
| 5,015,238 A | 5/1991 | Solomon et al. |
| 5,019,096 A | 5/1991 | Fox, Jr. et al. |
| 5,021,059 A | 6/1991 | Kensey et al. |
| 5,024,657 A | 6/1991 | Needham et al. |
| 5,025,001 A | 6/1991 | Loscalzo et al. |
| 5,026,359 A | 6/1991 | Burroughs |
| 5,031,622 A | 7/1991 | LaHaye |
| 5,033,961 A | 7/1991 | Kandler et al. |
| 5,047,021 A | 9/1991 | Utterberg |
| 5,049,139 A | 9/1991 | Gilchrist |
| 5,059,186 A | 10/1991 | Yamamoto et al. |
| 5,065,783 A | 11/1991 | Ogle, II |
| 5,070,885 A | 12/1991 | Bonaldo |
| 5,071,411 A | 12/1991 | Hillstead |
| 5,071,413 A | 12/1991 | Utterberg |
| 5,098,385 A | 3/1992 | Walsh |
| 5,108,376 A | 4/1992 | Bonaldo |
| 5,122,123 A | 6/1992 | Vaillancourt |
| 5,127,626 A | 7/1992 | Hilal et al. |
| 5,129,824 A | 7/1992 | Keller |
| 5,139,483 A | 8/1992 | Ryan |
| 5,143,104 A | 9/1992 | Iba et al. |
| 5,147,333 A | 9/1992 | Raines |
| 5,154,703 A | 10/1992 | Bonaldo |
| 5,154,920 A | 10/1992 | Flesher et al. |
| 5,184,742 A | 2/1993 | DeCaprio et al. |
| 5,190,534 A | 3/1993 | Kendell |
| 5,195,957 A | 3/1993 | Tollini |
| RE34,223 E | 4/1993 | Bonaldo |
| 5,199,948 A | 4/1993 | McPhee |
| 5,201,725 A | 4/1993 | Kling |
| 5,203,775 A | 4/1993 | Frank et al. |
| 5,205,820 A | 4/1993 | Kriesel |
| 5,205,821 A | 4/1993 | Kruger et al. |
| 5,207,706 A | 5/1993 | Menaker |
| 5,211,634 A | 5/1993 | Vaillancourt |
| 5,212,204 A | 5/1993 | Keefer et al. |
| 5,215,537 A | 6/1993 | Lynn et al. |
| 5,240,675 A | 8/1993 | Wilk et al. |
| 5,242,421 A | 9/1993 | Chan |
| 5,242,425 A | 9/1993 | White et al. |
| 5,246,011 A | 9/1993 | Caillouette |
| 5,250,550 A | 10/1993 | Keefer et al. |
| 5,251,873 A | 10/1993 | Atkinson et al. |
| D342,134 S | 12/1993 | Mongeon |
| 5,269,771 A | 12/1993 | Thomas et al. |
| 5,278,192 A | 1/1994 | Fung et al. |
| 5,281,206 A | 1/1994 | Lopez |
| 5,284,475 A | 2/1994 | Mackal |
| 5,295,657 A | 3/1994 | Atkinson |
| 5,297,310 A | 3/1994 | Cox et al. |
| 5,301,686 A | 4/1994 | Newman |
| 5,304,130 A | 4/1994 | Button |
| 5,306,243 A | 4/1994 | Bonaldo |
| 5,312,377 A | 5/1994 | Dalton |
| 5,324,270 A | 6/1994 | Kayan et al. |
| 5,324,647 A | 6/1994 | Rubens et al. |
| 5,330,235 A | 7/1994 | Wagner et al. |
| 5,330,426 A | 7/1994 | Kriesel et al. |
| 5,330,450 A | 7/1994 | Lopez |
| 5,330,899 A | 7/1994 | Devaughn et al. |
| 5,337,730 A | 8/1994 | Maguire |
| 5,344,414 A | 9/1994 | Lopez et al. |
| 5,352,410 A | 10/1994 | Hansen et al. |
| 5,354,267 A | 10/1994 | Niermann et al. |
| 5,356,396 A | 10/1994 | Wyatt et al. |
| 5,360,413 A | 11/1994 | Leason et al. |
| 5,366,505 A | 11/1994 | Farber |
| 5,366,997 A | 11/1994 | Keefer et al. |
| 5,370,614 A | 12/1994 | Amundson et al. |
| 5,370,636 A | 12/1994 | Von Witzleben |
| 5,370,640 A | 12/1994 | Kolff |
| 5,375,589 A | 12/1994 | Bhatta |
| 5,380,306 A | 1/1995 | Brinon |
| 5,380,758 A | 1/1995 | Stamler et al. |
| 5,391,150 A | 2/1995 | Richmond |
| 5,402,826 A | 4/1995 | Molnar et al. |
| 5,405,331 A | 4/1995 | Behnke et al. |
| 5,405,333 A | 4/1995 | Richmond |
| 5,405,919 A | 4/1995 | Keefer et al. |
| 5,407,807 A | 4/1995 | Markus |
| 5,409,012 A | 4/1995 | Sahatjian |
| 5,411,499 A | 5/1995 | Dudar et al. |
| 5,417,673 A | 5/1995 | Gordon |
| 5,425,465 A | 6/1995 | Healy |
| 5,428,070 A | 6/1995 | Cooke et al. |
| 5,433,330 A | 7/1995 | Yatsko et al. |
| 5,433,705 A | 7/1995 | Giebel et al. |
| 5,439,451 A | 8/1995 | Collinson et al. |
| 5,441,487 A | 8/1995 | Vedder |
| 5,445,623 A | 8/1995 | Richmond |
| 5,456,668 A | 10/1995 | Ogle, II |
| 5,456,675 A | 10/1995 | Wolbring et al. |
| 5,464,399 A | 11/1995 | Boettger |
| 5,470,307 A | 11/1995 | Lindall |
| 5,470,327 A | 11/1995 | Helgren et al. |
| 5,471,706 A | 12/1995 | Wallock et al. |
| 5,474,536 A | 12/1995 | Bonaldo |
| 5,480,393 A | 1/1996 | Bommarito |
| 5,492,147 A | 2/1996 | Challender et al. |
| 5,496,288 A | 3/1996 | Sweeney |
| 5,501,426 A | 3/1996 | Atkinson et al. |
| 5,507,733 A | 4/1996 | Larkin et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,485,827 A | 6/1996 | Zapol et al. |
| 5,525,357 A | 6/1996 | Keefer et al. |
| 5,531,695 A | 7/1996 | Swisher |
| 5,533,708 A | 7/1996 | Atkinson et al. |
| 5,533,983 A | 7/1996 | Haining |
| 5,535,785 A | 7/1996 | Werge et al. |
| 5,536,241 A | 7/1996 | Zapol |
| 5,536,258 A | 7/1996 | Folden |
| 5,540,661 A | 7/1996 | Tomisaka et al. |
| 5,545,614 A | 8/1996 | Stamler et al. |
| 5,549,566 A | 8/1996 | Elias et al. |
| 5,549,651 A | 8/1996 | Lynn |
| 5,552,115 A | 9/1996 | Malchesky |
| 5,552,118 A | 9/1996 | Mayer |
| 5,554,127 A | 9/1996 | Crouther et al. |
| 5,554,135 A * | 9/1996 | Menyhay ............. A61M 39/20 604/539 |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,580,530 A | 12/1996 | Kowatsch et al. |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,599,352 A | 2/1997 | Dinh et al. |
| 5,605,696 A | 2/1997 | Eury et al. |
| 5,607,072 A | 3/1997 | Rigney et al. |
| 5,613,615 A | 3/1997 | Zeyfang et al. |
| 5,616,130 A | 4/1997 | Mayer |
| 5,620,088 A | 4/1997 | Martin et al. |
| 5,620,427 A | 4/1997 | Werschmidt et al. |

(56) References Cited

U.S. PATENT DOCUMENTS

| | | |
|---|---|---|
| 5,624,402 A | 4/1997 | Imbert |
| 5,628,733 A | 5/1997 | Zinreich et al. |
| RE35,539 E | 6/1997 | Bonaldo |
| 5,645,538 A | 7/1997 | Richmond |
| 5,665,077 A | 9/1997 | Resen et al. |
| 5,674,206 A | 10/1997 | Allton et al. |
| 5,676,346 A | 10/1997 | Leinsing |
| 5,685,835 A | 11/1997 | Brugger |
| 5,685,866 A | 11/1997 | Lopez |
| 5,685,868 A | 11/1997 | Lundquist |
| 5,688,253 A | 11/1997 | Lundquist |
| 5,694,978 A | 12/1997 | Heilmann et al. |
| 5,699,821 A | 12/1997 | Paradis |
| 5,700,248 A | 12/1997 | Lopez |
| 5,702,017 A | 12/1997 | Goncalves |
| 5,716,339 A | 2/1998 | Tanaka et al. |
| 5,722,537 A | 3/1998 | Sigler |
| 5,735,826 A | 4/1998 | Richmond |
| 5,738,144 A | 4/1998 | Rogers |
| 5,743,892 A | 4/1998 | Loh et al. |
| 5,749,861 A | 5/1998 | Guala et al. |
| 5,763,409 A | 6/1998 | Bayol et al. |
| 5,770,645 A | 6/1998 | Stamler et al. |
| 5,776,116 A | 7/1998 | Lopez |
| 5,782,808 A | 7/1998 | Folden |
| 5,782,816 A | 7/1998 | Werschmidt et al. |
| 5,785,693 A | 7/1998 | Haining |
| 5,792,120 A | 8/1998 | Menyhay |
| 5,797,887 A | 8/1998 | Rosen et al. |
| 5,806,831 A | 9/1998 | Paradis |
| 5,810,792 A | 9/1998 | Fangrow, Jr. et al. |
| 5,814,024 A | 9/1998 | Thompson et al. |
| 5,814,666 A | 9/1998 | Green et al. |
| 5,820,601 A | 10/1998 | Mayer |
| 5,820,604 A | 10/1998 | Fox et al. |
| 5,827,244 A | 10/1998 | Boettger |
| 5,839,715 A | 11/1998 | Leinsing |
| 5,848,994 A | 12/1998 | Richmond |
| 5,902,631 A | 5/1999 | Wang et al. |
| 5,941,857 A | 8/1999 | Nguyen et al. |
| 5,947,296 A | 9/1999 | Castora |
| 5,947,954 A | 9/1999 | Bonaldo |
| 5,951,519 A | 9/1999 | Utterberg |
| 5,954,957 A | 9/1999 | Chin-Loy et al. |
| 5,971,972 A | 10/1999 | Rosenbaum |
| D416,086 S | 11/1999 | Parris et al. |
| 5,989,229 A | 11/1999 | Chiappetta |
| 5,994,444 A | 11/1999 | Trescony |
| 5,996,779 A | 12/1999 | Klardie et al. |
| 6,029,946 A | 2/2000 | Doyle |
| 6,036,171 A | 3/2000 | Weinheimer et al. |
| 6,041,805 A | 3/2000 | Gydesen et al. |
| 6,045,539 A | 4/2000 | Menyhay |
| 6,045,623 A | 4/2000 | Cannon |
| 6,050,978 A | 4/2000 | Orr et al. |
| 6,059,107 A | 5/2000 | Nosted et al. |
| 6,063,062 A | 5/2000 | Paradis |
| 6,068,011 A | 5/2000 | Paradis |
| 6,068,475 A | 5/2000 | Stoyka, Jr. et al. |
| 6,068,617 A | 5/2000 | Richmond |
| 6,071,413 A | 6/2000 | Dyke |
| 6,079,432 A | 6/2000 | Paradis |
| 6,087,479 A | 7/2000 | Stamler et al. |
| 6,093,743 A | 7/2000 | Lai et al. |
| 6,095,356 A | 8/2000 | Rits |
| 6,099,519 A | 8/2000 | Olsen et al. |
| 6,105,812 A | 8/2000 | Riordan |
| 6,106,502 A | 8/2000 | Richmond |
| 6,113,068 A | 9/2000 | Ryan |
| 6,113,572 A | 9/2000 | Gailey et al. |
| 6,116,468 A | 9/2000 | Nilson |
| 6,117,114 A | 9/2000 | Paradis |
| 6,126,640 A | 10/2000 | Tucker et al. |
| 6,142,446 A | 11/2000 | Leinsing |
| 6,143,318 A | 11/2000 | Gilchrist et al. |
| 6,146,363 A | 11/2000 | Giebel et al. |
| 6,152,913 A | 11/2000 | Feith et al. |
| 6,158,614 A | 12/2000 | Haines et al. |
| 6,170,522 B1 | 1/2001 | Tanida |
| 6,171,287 B1 | 1/2001 | Lynn et al. |
| 6,174,539 B1 | 1/2001 | Stamler et al. |
| 6,179,141 B1 | 1/2001 | Nakamura |
| 6,183,450 B1 | 2/2001 | Lois |
| 6,202,870 B1 | 3/2001 | Pearce |
| 6,202,901 B1 | 3/2001 | Gerber et al. |
| 6,206,134 B1 | 3/2001 | Stark et al. |
| 6,206,860 B1 | 3/2001 | Richmond |
| 6,207,855 B1 | 3/2001 | Toone et al. |
| 6,217,564 B1 | 4/2001 | Peters et al. |
| 6,227,391 B1 | 5/2001 | King |
| 6,232,406 B1 | 5/2001 | Stoy |
| 6,232,434 B1 | 5/2001 | Stamler et al. |
| 6,237,800 B1 | 5/2001 | Barrett et al. |
| 6,242,393 B1 | 6/2001 | Ishida et al. |
| 6,245,048 B1 | 6/2001 | Fangrow et al. |
| 6,245,056 B1 | 6/2001 | Walker et al. |
| 6,248,380 B1 | 6/2001 | Kocher et al. |
| 6,250,315 B1 | 6/2001 | Ernster |
| 6,255,277 B1 | 7/2001 | Stamler et al. |
| 6,267,754 B1 | 7/2001 | Peters |
| 6,299,132 B1 | 10/2001 | Weinheimer et al. |
| 6,315,113 B1 | 11/2001 | Britton et al. |
| 6,315,761 B1 | 11/2001 | Shcherbina et al. |
| 6,359,167 B2 | 3/2002 | Toone et al. |
| 6,359,182 B1 | 3/2002 | Stamler et al. |
| 6,375,231 B1 | 4/2002 | Picha et al. |
| 6,379,660 B1 | 4/2002 | Saavedra et al. |
| 6,379,691 B1 | 4/2002 | Tedeschi et al. |
| 6,394,983 B1 | 5/2002 | Mayoral et al. |
| 6,402,207 B1 | 6/2002 | Segal et al. |
| 6,403,759 B2 | 6/2002 | Stamler et al. |
| 6,409,716 B1 | 6/2002 | Sahatjian et al. |
| 6,428,520 B1 | 8/2002 | Lopez |
| 6,431,219 B1 | 8/2002 | Redler et al. |
| 6,444,318 B1 | 9/2002 | Guire et al. |
| 6,468,259 B1 | 10/2002 | Djokic et al. |
| 6,471,978 B1 | 10/2002 | Stamler et al. |
| 6,488,951 B2 | 12/2002 | Toone et al. |
| 6,491,965 B1 | 12/2002 | Berry et al. |
| 6,499,719 B1 | 12/2002 | Clancy et al. |
| 6,508,792 B2 | 1/2003 | Szames et al. |
| 6,508,807 B1 | 1/2003 | Peters |
| 6,538,116 B2 | 3/2003 | Stamler et al. |
| 6,541,802 B2 | 4/2003 | Doyle |
| 6,543,745 B1 | 4/2003 | Enerson |
| 6,550,493 B2 | 4/2003 | Williamson et al. |
| 6,555,504 B1 | 4/2003 | Ayai et al. |
| 6,562,781 B1 | 5/2003 | Berry et al. |
| 6,581,906 B2 | 6/2003 | Pott et al. |
| 6,583,311 B2 | 6/2003 | Toone et al. |
| 6,585,691 B1 | 7/2003 | Vitello |
| 6,595,964 B2 | 7/2003 | Finley et al. |
| 6,595,981 B2 | 7/2003 | Huet |
| 6,605,294 B2 | 8/2003 | Sawhney |
| 6,605,751 B1 | 8/2003 | Gibbins et al. |
| 6,609,696 B2 | 8/2003 | Enerson |
| 6,632,199 B1 | 10/2003 | Tucker et al. |
| 6,634,498 B2 | 10/2003 | Kayerod et al. |
| 6,656,217 B1 | 12/2003 | Herzog, Jr. et al. |
| 6,666,852 B2 | 12/2003 | Niedospial, Jr. |
| 6,673,891 B2 | 1/2004 | Stamler et al. |
| 6,679,395 B1 | 1/2004 | Pfefferkorn et al. |
| 6,679,870 B1 | 1/2004 | Finch et al. |
| 6,681,803 B2 | 1/2004 | Taneya et al. |
| 6,685,694 B2 | 2/2004 | Finch et al. |
| 6,692,468 B1 | 2/2004 | Waldenburg |
| 6,695,817 B1 | 2/2004 | Fangrow |
| 6,716,396 B1 | 4/2004 | Anderson |
| 6,722,705 B2 | 4/2004 | Korkor |
| 6,725,492 B2 | 4/2004 | Moore et al. |
| 6,745,998 B2 | 6/2004 | Doyle |
| 6,786,884 B1 | 9/2004 | DeCant, Jr. et al. |
| 6,808,510 B1 | 10/2004 | DiFiore |
| 6,827,766 B2 | 12/2004 | Carnes et al. |

(56) References Cited

U.S. PATENT DOCUMENTS

| | | |
|---|---|---|
| 6,840,501 B2 | 1/2005 | Doyle |
| 6,871,087 B1 | 3/2005 | Hughes et al. |
| 6,875,205 B2 | 4/2005 | Leinsing |
| 6,875,840 B2 | 4/2005 | Stamler et al. |
| 6,880,706 B2 | 4/2005 | Braconnot et al. |
| 6,887,994 B2 | 5/2005 | Stamler et al. |
| 6,899,315 B2 | 5/2005 | Mailville et al. |
| 6,911,025 B2 | 6/2005 | Miyahar |
| 6,916,051 B2 | 7/2005 | Fisher |
| 6,929,005 B2 | 8/2005 | Sullivan et al. |
| 6,943,035 B1 | 9/2005 | Davies et al. |
| 6,955,669 B2 | 10/2005 | Curutcharry |
| 6,964,406 B2 | 11/2005 | Doyle |
| 7,004,934 B2 | 2/2006 | Vaillancourt |
| 7,015,347 B2 | 3/2006 | Toone et al. |
| 7,030,238 B2 | 4/2006 | Stamler et al. |
| 7,037,302 B2 | 5/2006 | Vaillancourt |
| 7,040,598 B2 | 5/2006 | Raybuck |
| 7,044,441 B2 | 5/2006 | Doyle |
| 7,045,585 B2 | 5/2006 | Berry et al. |
| 7,049,308 B2 | 5/2006 | Stamler et al. |
| 7,052,711 B2 | 5/2006 | West et al. |
| 7,056,308 B2 | 6/2006 | Utterberg |
| 7,067,659 B2 | 6/2006 | Stamler et al. |
| 7,081,109 B2 | 7/2006 | Tighe et al. |
| 7,083,605 B2 | 8/2006 | Miyahara |
| 7,087,709 B2 | 8/2006 | Stamler et al. |
| 7,097,850 B2 | 8/2006 | Chappa et al. |
| 7,100,891 B2 | 9/2006 | Doyle |
| 7,125,396 B2 | 10/2006 | Leinsing et al. |
| 7,140,592 B2 | 11/2006 | Phillips |
| 7,147,625 B2 | 12/2006 | Sarangapani et al. |
| 7,160,272 B1 | 1/2007 | Eyal et al. |
| 7,182,313 B2 | 2/2007 | Doyle |
| 7,195,615 B2 | 3/2007 | Tan |
| 7,198,611 B2 | 4/2007 | Connell et al. |
| 7,244,249 B2 | 7/2007 | Leinsing et al. |
| 7,259,250 B2 | 8/2007 | Stamler et al. |
| 7,279,176 B1 | 10/2007 | West et al. |
| 7,282,186 B2 | 10/2007 | Lake, Jr. et al. |
| 7,306,197 B2 | 12/2007 | Parrino et al. |
| 7,306,198 B2 | 12/2007 | Doyle |
| 7,306,566 B2 | 12/2007 | Raybuck |
| 7,309,326 B2 | 12/2007 | Fangrow, Jr. |
| 7,316,669 B2 | 1/2008 | Ranalletta |
| 7,347,458 B2 | 3/2008 | Rome et al. |
| 7,347,853 B2 | 3/2008 | DiFiore et al. |
| 7,350,764 B2 | 4/2008 | Raybuck |
| 7,361,164 B2 | 4/2008 | Simpson et al. |
| 7,417,109 B2 | 8/2008 | Stamler et al. |
| 7,431,712 B2 | 10/2008 | Kim |
| 7,442,402 B2 | 10/2008 | Chudzik et al. |
| 7,452,349 B2 | 11/2008 | Miyahar |
| 7,485,107 B2 | 2/2009 | DiFiore et al. |
| 7,491,192 B2 | 2/2009 | DiFiore |
| 7,497,484 B2 | 3/2009 | Ziman |
| 7,516,846 B2 | 4/2009 | Hansen |
| 7,588,563 B2 | 9/2009 | Guala |
| 7,611,505 B2 | 11/2009 | Ranalletta et al. |
| 7,614,426 B2 | 11/2009 | Kitani et al. |
| 7,615,034 B2 | 11/2009 | DiFiore |
| 7,625,907 B2 | 12/2009 | Stamler et al. |
| 7,635,344 B2 | 12/2009 | Tennican et al. |
| D607,325 S | 1/2010 | Rogers et al. |
| 7,645,274 B2 | 1/2010 | Whitley |
| 7,651,481 B2 | 1/2010 | Raybuck |
| 7,666,170 B2 | 2/2010 | Guala |
| 7,708,714 B2 | 5/2010 | Connell et al. |
| 7,731,678 B2 | 6/2010 | Tennican et al. |
| 7,731,679 B2 | 6/2010 | Tennican et al. |
| 7,749,189 B2 | 7/2010 | Tennican et al. |
| 7,753,891 B2 | 7/2010 | Tennican et al. |
| 7,758,530 B2 | 7/2010 | DiFiore et al. |
| 7,758,566 B2 | 7/2010 | Simpson et al. |
| 7,762,524 B2 | 7/2010 | Cawthon et al. |
| 7,763,006 B2 | 7/2010 | Tennican |
| 7,766,182 B2 | 8/2010 | Trent et al. |
| 7,766,897 B2 | 8/2010 | Ramsey et al. |
| 7,776,011 B2 | 8/2010 | Tennican et al. |
| 7,780,794 B2 | 8/2010 | Rogers et al. |
| 7,785,616 B2 | 8/2010 | Stamler et al. |
| 7,794,675 B2 | 9/2010 | Lynn |
| 7,799,010 B2 | 9/2010 | Tennican |
| 7,803,139 B2 | 9/2010 | Fangrow, Jr. |
| 7,803,140 B2 | 9/2010 | Fangrow, Jr. |
| 7,815,614 B2 | 10/2010 | Fangrow, Jr. |
| 7,857,793 B2 | 12/2010 | Raulerson et al. |
| 7,922,701 B2 | 4/2011 | Buchman |
| 7,922,711 B2 | 4/2011 | Ranalletta et al. |
| 7,928,079 B2 | 4/2011 | Hrabie et al. |
| 7,938,795 B2 | 5/2011 | DiFiore et al. |
| 7,956,062 B2 | 6/2011 | Stamler et al. |
| 7,959,026 B2 | 6/2011 | Bertani |
| 7,963,565 B2 | 6/2011 | Suter |
| 7,972,137 B2 | 7/2011 | Rosen |
| 7,972,322 B2 | 7/2011 | Tennican |
| 7,981,090 B2 | 7/2011 | Plishka et al. |
| 7,985,302 B2 | 7/2011 | Rogers et al. |
| 7,993,309 B2 | 8/2011 | Schweikert |
| 7,998,134 B2 | 8/2011 | Fangrow et al. |
| 8,034,454 B2 | 10/2011 | Terry |
| 8,065,773 B2 | 11/2011 | Vaillancourt et al. |
| 8,066,670 B2 | 11/2011 | Cluff et al. |
| 8,069,523 B2 | 12/2011 | Vaillancourt et al. |
| 8,113,837 B2 | 2/2012 | Zegarelli |
| 8,146,757 B2 | 4/2012 | Abreu et al. |
| 8,162,899 B2 | 4/2012 | Tennican |
| 8,167,847 B2 | 5/2012 | Anderson et al. |
| 8,172,825 B2 | 5/2012 | Solomon et al. |
| 8,177,761 B2 | 5/2012 | Howlett et al. |
| 8,177,772 B2 | 5/2012 | Christensen et al. |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,231,602 B2 | 7/2012 | Anderson et al. |
| 8,252,247 B2 | 8/2012 | Ferlic |
| 8,262,628 B2 | 9/2012 | Fangrow, Jr. |
| 8,262,643 B2 | 9/2012 | Tennican |
| 8,273,303 B2 | 9/2012 | Ferlic et al. |
| 8,281,824 B2 | 10/2012 | Molema et al. |
| 8,328,767 B2 | 12/2012 | Solomon et al. |
| 8,336,152 B2 | 12/2012 | Kerr et al. |
| 8,343,112 B2 | 1/2013 | Solomon et al. |
| 8,361,408 B2 | 1/2013 | Lynn |
| 8,372,045 B2 | 2/2013 | Needle et al. |
| 8,377,040 B2 | 2/2013 | Burkholz et al. |
| 8,414,547 B2 | 4/2013 | DiFiore et al. |
| 8,454,579 B2 | 6/2013 | Fangrow, Jr. |
| 8,480,968 B2 | 7/2013 | Lynn |
| 8,491,546 B2 | 7/2013 | Hoang et al. |
| 8,500,717 B2 | 8/2013 | Becker |
| 8,506,527 B2 | 8/2013 | Carlyon |
| 8,506,538 B2 | 8/2013 | Chelak |
| 8,523,798 B2 | 9/2013 | DiFiore |
| 8,523,831 B2 | 9/2013 | Solomon et al. |
| 8,533,887 B2 | 9/2013 | Hirst |
| 8,545,479 B2 | 10/2013 | Kitani et al. |
| 8,568,371 B2 | 10/2013 | Siopes et al. |
| 8,622,995 B2 | 1/2014 | Ziebol et al. |
| 8,622,996 B2 | 1/2014 | Ziebol et al. |
| 8,641,684 B2 | 2/2014 | Utterberg et al. |
| 8,647,308 B2 | 2/2014 | Solomon et al. |
| 8,647,326 B2 | 2/2014 | Solomon et al. |
| 8,651,271 B1 | 2/2014 | Shen |
| 8,740,864 B2 | 6/2014 | Hoang et al. |
| 8,758,307 B2 | 6/2014 | Grimm et al. |
| 8,777,504 B2 | 7/2014 | Shaw et al. |
| 8,791,073 B2 | 7/2014 | West et al. |
| 8,845,593 B2 | 9/2014 | Anderson et al. |
| 8,877,231 B2 | 11/2014 | Rosen |
| 8,910,919 B2 | 12/2014 | Bonnal et al. |
| 8,920,404 B2 | 12/2014 | DiFiore et al. |
| 8,968,268 B2 | 3/2015 | Anderson et al. |
| 8,981,139 B2 | 3/2015 | Schoenfisch et al. |

(56) References Cited

U.S. PATENT DOCUMENTS

| | | |
|---|---|---|
| 8,999,073 B2 | 4/2015 | Rogers et al. |
| 9,022,984 B2 | 5/2015 | Ziebol et al. |
| 9,072,296 B2 | 7/2015 | Mills et al. |
| 9,072,868 B2 | 7/2015 | Ziebol et al. |
| 9,078,992 B2 | 7/2015 | Ziebol et al. |
| 9,089,680 B2 | 7/2015 | Ueda et al. |
| 9,101,685 B2 | 8/2015 | Li et al. |
| 9,149,624 B2 | 10/2015 | Lewis |
| 9,192,449 B2 | 11/2015 | Kerr et al. |
| 9,205,248 B2 | 12/2015 | Wu et al. |
| 9,248,093 B2 | 2/2016 | Kelley, III et al. |
| 9,248,229 B2 | 2/2016 | Devouassoux et al. |
| 9,259,284 B2 | 2/2016 | Rogers et al. |
| 9,259,535 B2 | 2/2016 | Anderson et al. |
| 9,283,367 B2 | 3/2016 | Hoang et al. |
| 9,283,368 B2 | 3/2016 | Hoang et al. |
| 9,296,525 B2 | 3/2016 | Murphy et al. |
| 9,302,049 B2 | 4/2016 | Tekeste |
| 9,320,858 B2 | 4/2016 | Grimm et al. |
| 9,320,859 B2 | 4/2016 | Grimm et al. |
| 9,320,860 B2 | 4/2016 | Grimm et al. |
| 9,352,080 B2 | 5/2016 | Goodall et al. |
| 9,352,142 B2 | 5/2016 | Ziebol et al. |
| 9,381,339 B2 | 7/2016 | Wu et al. |
| 9,399,125 B2 | 7/2016 | Burkholz |
| 9,527,660 B2 | 12/2016 | Tennican |
| 9,592,375 B2 | 3/2017 | Tennican |
| 9,700,676 B2 | 7/2017 | Anderson et al. |
| 9,700,677 B2 | 7/2017 | Anderson et al. |
| 9,700,710 B2 | 7/2017 | Anderson et al. |
| 9,707,348 B2 | 7/2017 | Anderson et al. |
| 9,707,349 B2 | 7/2017 | Anderson et al. |
| 9,707,350 B2 | 7/2017 | Anderson et al. |
| 9,809,355 B2 | 11/2017 | Solomon et al. |
| 9,849,276 B2 | 12/2017 | Ziebol et al. |
| 9,867,975 B2 | 1/2018 | Gardner et al. |
| 9,907,617 B2 | 3/2018 | Rogers |
| 9,933,094 B2 | 4/2018 | Fangrow |
| 9,999,471 B2 | 6/2018 | Rogers et al. |
| 10,016,587 B2 | 7/2018 | Gardner et al. |
| 10,046,156 B2 | 8/2018 | Gardner et al. |
| 10,159,829 B2 | 12/2018 | Ziebol et al. |
| 10,166,381 B2 | 1/2019 | Gardner et al. |
| 10,195,000 B2 | 2/2019 | Rogers et al. |
| 10,201,692 B2 | 2/2019 | Chang |
| 10,328,207 B2 | 6/2019 | Anderson et al. |
| 10,524,982 B2 | 1/2020 | Fangrow |
| 10,525,250 B1 | 1/2020 | Ziebol et al. |
| 10,695,550 B2 | 6/2020 | Gardner et al. |
| 10,744,316 B2 | 8/2020 | Fangrow |
| 10,806,919 B2 | 10/2020 | Gardner et al. |
| 10,821,278 B2 | 11/2020 | Gardner et al. |
| 11,160,932 B2 | 11/2021 | Anderson et al. |
| 11,229,746 B2 | 1/2022 | Anderson et al. |
| 11,351,353 B2 | 6/2022 | Ziebol et al. |
| 11,389,634 B2 | 7/2022 | Ziebol et al. |
| 11,400,195 B2 | 8/2022 | Ziebol et al. |
| 11,433,215 B2 | 9/2022 | Ziebol et al. |
| 11,497,904 B2 | 11/2022 | Fangrow et al. |
| 11,517,732 B2 | 12/2022 | Ziebol et al. |
| 11,517,733 B2 | 12/2022 | Fangrow |
| 11,534,595 B2 | 12/2022 | Ziebol et al. |
| 11,541,220 B2 | 1/2023 | Ziebol et al. |
| 11,541,221 B2 | 1/2023 | Ziebol et al. |
| 11,559,467 B2 | 1/2023 | Fangrow |
| 11,684,720 B2 | 6/2023 | Anderson et al. |
| 2002/0077693 A1 | 6/2002 | Barclay et al. |
| 2002/0082682 A1 | 6/2002 | Barclay et al. |
| 2002/0098278 A1 | 6/2002 | Bates et al. |
| 2003/0039697 A1 | 2/2003 | Zhao et al. |
| 2003/0062376 A1 | 4/2003 | Sears et al. |
| 2003/0072783 A1 | 4/2003 | Stamler et al. |
| 2003/0153865 A1* | 8/2003 | Connell ............ A61M 39/20 604/28 |
| 2003/0199835 A1 | 10/2003 | Leinsing et al. |
| 2003/0208165 A1 | 11/2003 | Christensen et al. |
| 2004/0034042 A1 | 2/2004 | Tsuji et al. |
| 2004/0034329 A1 | 2/2004 | Mankus et al. |
| 2004/0037836 A1 | 2/2004 | Stamler et al. |
| 2004/0048542 A1 | 3/2004 | Thomaschefsky et al. |
| 2004/0052689 A1 | 3/2004 | Yao |
| 2004/0052831 A1 | 3/2004 | Modak et al. |
| 2004/0156908 A1 | 8/2004 | Polaschegg et al. |
| 2004/0210201 A1 | 10/2004 | Farnan |
| 2004/0215148 A1 | 10/2004 | Hwang et al. |
| 2004/0247640 A1 | 12/2004 | Zhao et al. |
| 2004/0249337 A1 | 12/2004 | DiFiore |
| 2004/0249338 A1 | 12/2004 | DeCant, Jr. et al. |
| 2004/0258560 A1 | 12/2004 | Lake, Jr. et al. |
| 2005/0013836 A1 | 1/2005 | Raad |
| 2005/0015075 A1 | 1/2005 | Wright et al. |
| 2005/0065479 A1 | 3/2005 | Schiller et al. |
| 2005/0098527 A1 | 5/2005 | Yates et al. |
| 2005/0124942 A1 | 6/2005 | Richmond |
| 2005/0124970 A1 | 6/2005 | Kunin et al. |
| 2005/0147524 A1 | 7/2005 | Bousquet |
| 2005/0147525 A1 | 7/2005 | Bousquet |
| 2005/0148930 A1 | 7/2005 | Hseih et al. |
| 2005/0152891 A1 | 7/2005 | Toone et al. |
| 2005/0171493 A1 | 8/2005 | Nicholls |
| 2005/0214185 A1 | 9/2005 | Castaneda |
| 2005/0220882 A1 | 10/2005 | Pritchard et al. |
| 2005/0228362 A1 | 10/2005 | Vaillancourt |
| 2005/0228482 A1 | 10/2005 | Herzog et al. |
| 2005/0256461 A1 | 11/2005 | DiFiore et al. |
| 2005/0265958 A1 | 12/2005 | West et al. |
| 2005/0267421 A1 | 12/2005 | Wing |
| 2005/0271711 A1 | 12/2005 | Lynch et al. |
| 2005/0288551 A1 | 12/2005 | Callister et al. |
| 2006/0004316 A1 | 1/2006 | DiFiore et al. |
| 2006/0024372 A1 | 2/2006 | Utterberg et al. |
| 2006/0030827 A1 | 2/2006 | Raulerson et al. |
| 2006/0058734 A1 | 3/2006 | Phillips |
| 2006/0096348 A1 | 5/2006 | DiFiore |
| 2006/0118122 A1 | 6/2006 | Martens et al. |
| 2006/0129109 A1 | 6/2006 | Shaw et al. |
| 2006/0142730 A1 | 6/2006 | Proulx et al. |
| 2006/0149191 A1 | 7/2006 | DiFiore |
| 2006/0161115 A1 | 7/2006 | Fangrow |
| 2006/0195117 A1 | 8/2006 | Rucker et al. |
| 2006/0202146 A1 | 9/2006 | Doyle |
| 2006/0206178 A1 | 9/2006 | Kim |
| 2006/0253084 A1 | 11/2006 | Nordgren |
| 2006/0261076 A1 | 11/2006 | Anderson |
| 2007/0003603 A1 | 1/2007 | Karandikar et al. |
| 2007/0088292 A1 | 4/2007 | Fangrow |
| 2007/0088293 A1 | 4/2007 | Fangrow |
| 2007/0088294 A1 | 4/2007 | Fangrow |
| 2007/0106205 A1 | 5/2007 | Connell et al. |
| 2007/0112333 A1 | 5/2007 | Hoang et al. |
| 2007/0156118 A1 | 7/2007 | Ramsey et al. |
| 2007/0167910 A1 | 7/2007 | Tennican et al. |
| 2007/0176117 A1 | 8/2007 | Redmond et al. |
| 2007/0179453 A1 | 8/2007 | Lim et al. |
| 2007/0187353 A1 | 8/2007 | Fox et al. |
| 2007/0202177 A1 | 8/2007 | Hoang |
| 2007/0212381 A1 | 9/2007 | DiFiore et al. |
| 2007/0231315 A1 | 10/2007 | Lichte et al. |
| 2007/0248676 A1 | 10/2007 | Stamler et al. |
| 2007/0249996 A1 | 10/2007 | Tennican et al. |
| 2007/0265578 A1 | 11/2007 | Tennican et al. |
| 2007/0282280 A1 | 12/2007 | Tennican |
| 2007/0287989 A1 | 12/2007 | Crawford et al. |
| 2008/0027399 A1 | 1/2008 | Harding et al. |
| 2008/0027401 A1 | 1/2008 | Ou-Yang |
| 2008/0033371 A1 | 2/2008 | Updegraff et al. |
| 2008/0039803 A1 | 2/2008 | Lynn |
| 2008/0058733 A1 | 3/2008 | Vogt et al. |
| 2008/0093245 A1 | 4/2008 | Periasamy et al. |
| 2008/0095680 A1 | 4/2008 | Steffens et al. |
| 2008/0097315 A1 | 4/2008 | Miner et al. |
| 2008/0097407 A1 | 4/2008 | Plishka |
| 2008/0103485 A1 | 5/2008 | Kruger |
| 2008/0287920 A1 | 5/2008 | Fangrow et al. |

(56) References Cited

U.S. PATENT DOCUMENTS

| | | |
|---|---|---|
| 2008/0014005 A1 | 6/2008 | Shirley |
| 2008/0128646 A1 | 6/2008 | Clawson |
| 2008/0132880 A1 | 6/2008 | Buchman |
| 2008/0147047 A1 | 6/2008 | Davis et al. |
| 2008/0161763 A1 | 7/2008 | Harding et al. |
| 2008/0172007 A1 | 7/2008 | Bousquet |
| 2008/0173651 A1 | 7/2008 | Ping |
| 2008/0177250 A1 | 7/2008 | Howlett et al. |
| 2008/0187460 A1 | 8/2008 | Utterberg et al. |
| 2008/0188791 A1 | 8/2008 | DiFiore et al. |
| 2008/0190485 A1 | 8/2008 | Guala |
| 2008/0235888 A1 | 10/2008 | Vaillancourt et al. |
| 2008/0262465 A1 | 10/2008 | Zinger et al. |
| 2008/0318333 A1 | 12/2008 | Nielsen et al. |
| 2008/0319423 A1 | 12/2008 | Tanghoj et al. |
| 2009/0008393 A1 | 1/2009 | Howlett et al. |
| 2009/0012426 A1 | 1/2009 | Tennican |
| 2009/0024096 A1 | 1/2009 | Hai et al. |
| 2009/0028750 A1 | 1/2009 | Ryan |
| 2009/0062766 A1 | 3/2009 | Howlett et al. |
| 2009/0093757 A1 | 4/2009 | Tennican |
| 2009/0099529 A1 | 4/2009 | Anderson et al. |
| 2009/0126867 A1 | 5/2009 | Decant, Jr. et al. |
| 2009/0137969 A1 | 5/2009 | Colantonio et al. |
| 2009/0149820 A1 | 6/2009 | DiFiore |
| 2009/0163876 A1 | 6/2009 | Chebator et al. |
| 2009/0205151 A1 | 8/2009 | Fisher et al. |
| 2009/0205656 A1 | 8/2009 | Nishibayashi et al. |
| 2009/0247485 A1 | 10/2009 | Ahmed et al. |
| 2009/0259194 A1 | 10/2009 | Pinedjian et al. |
| 2009/0270832 A1 | 10/2009 | Vancaillie et al. |
| 2009/0293882 A1 | 12/2009 | Terry |
| 2010/0004510 A1 | 1/2010 | Kuroshima |
| 2010/0049170 A1 | 2/2010 | Solomon et al. |
| 2010/0050351 A1 | 3/2010 | Colantonio et al. |
| 2010/0064456 A1 | 3/2010 | Ferlic |
| 2010/0074932 A1 | 3/2010 | Talsma |
| 2010/0137472 A1 | 6/2010 | Ou-Yang |
| 2010/0143427 A1 | 6/2010 | King et al. |
| 2010/0152670 A1 | 6/2010 | Low |
| 2010/0160894 A1 | 6/2010 | Julian et al. |
| 2010/0172794 A1 | 7/2010 | Ferlic et al. |
| 2010/0242993 A1 | 9/2010 | Hoang et al. |
| 2010/0253070 A1 | 10/2010 | Cheon et al. |
| 2010/0280805 A1 | 11/2010 | DiFiore |
| 2010/0292673 A1 | 11/2010 | Korogi et al. |
| 2010/0292674 A1 | 11/2010 | Jepson et al. |
| 2010/0306938 A1 | 12/2010 | Rogers et al. |
| 2010/0318040 A1 | 12/2010 | Kelley, III et al. |
| 2011/0030726 A1 | 2/2011 | Vaillancourt et al. |
| 2011/0044850 A1 | 2/2011 | Solomon et al. |
| 2011/0046564 A1 | 2/2011 | Zhong |
| 2011/0046603 A1 | 2/2011 | Felsovalyi et al. |
| 2011/0062703 A1 | 3/2011 | Lopez |
| 2011/0064512 A1 | 3/2011 | Shaw et al. |
| 2011/0071475 A1 | 3/2011 | Horvath et al. |
| 2011/0082431 A1 | 4/2011 | Burgess et al. |
| 2011/0175347 A1 | 7/2011 | Okiyama |
| 2011/0184338 A1 | 7/2011 | McKay |
| 2011/0184382 A1 | 7/2011 | Cady |
| 2011/0208128 A1 | 8/2011 | Wu et al. |
| 2011/0232020 A1 | 9/2011 | Rogers et al. |
| 2011/0265825 A1 | 11/2011 | Rogers et al. |
| 2011/0276031 A1 | 11/2011 | Hoang et al. |
| 2011/0277788 A1 | 11/2011 | Rogers et al. |
| 2011/0282302 A1 | 11/2011 | Lopez et al. |
| 2011/0290799 A1 | 12/2011 | Anderson et al. |
| 2011/0314619 A1 | 12/2011 | Schweikert |
| 2012/0022469 A1 | 1/2012 | Albert et al. |
| 2012/0029483 A1 | 2/2012 | Griffith et al. |
| 2012/0031904 A1 | 2/2012 | Kuhn et al. |
| 2012/0039764 A1 | 2/2012 | Solomon et al. |
| 2012/0083730 A1 | 4/2012 | Rush et al. |
| 2012/0083750 A1 | 4/2012 | Sansoucy |
| 2012/0157965 A1 | 6/2012 | Wotton et al. |
| 2012/0191029 A1 | 7/2012 | Hopf et al. |
| 2012/0195807 A1 | 8/2012 | Ferlic |
| 2012/0216359 A1 | 8/2012 | Rogers et al. |
| 2012/0216360 A1 | 8/2012 | Rogers et al. |
| 2012/0220955 A1 | 8/2012 | Maseda et al. |
| 2012/0283693 A1 | 11/2012 | Anderson et al. |
| 2012/0283696 A1 | 11/2012 | Cronenberg et al. |
| 2012/0296284 A1 | 11/2012 | Anderson et al. |
| 2012/0302968 A1 | 11/2012 | Tennican |
| 2012/0302970 A1 | 11/2012 | Tennican |
| 2012/0302997 A1 | 11/2012 | Gardner et al. |
| 2012/0315201 A1 | 12/2012 | Ferlic et al. |
| 2013/0006194 A1 | 1/2013 | Anderson et al. |
| 2013/0023828 A1 | 1/2013 | Anderson et al. |
| 2013/0030414 A1 | 1/2013 | Gardner et al. |
| 2013/0035667 A1 | 2/2013 | Anderson et al. |
| 2013/0039953 A1 | 2/2013 | Dudnyk et al. |
| 2013/0053751 A1 | 2/2013 | Holtham |
| 2013/0072908 A1 | 3/2013 | Solomon et al. |
| 2013/0085313 A1 | 4/2013 | Fowler et al. |
| 2013/0085474 A1 | 4/2013 | Charles et al. |
| 2013/0098938 A1 | 4/2013 | Efthimiadis |
| 2013/0102950 A1 | 4/2013 | DiFiore |
| 2013/0123754 A1 | 5/2013 | Solomon et al. |
| 2013/0134161 A1 | 5/2013 | Fogel et al. |
| 2013/0138085 A1 | 5/2013 | Tennican |
| 2013/0144258 A1 | 6/2013 | Ziebol et al. |
| 2013/0150795 A1 | 6/2013 | Snow |
| 2013/0164189 A1 | 6/2013 | Hadden |
| 2013/0171030 A1 | 7/2013 | Ferlic et al. |
| 2013/0183635 A1 | 7/2013 | Wilhoit |
| 2013/0197485 A1 | 8/2013 | Gardner et al. |
| 2014/0042116 A1 | 2/2014 | Shen et al. |
| 2014/0048079 A1 | 2/2014 | Gardner et al. |
| 2014/0052074 A1 | 2/2014 | Tekeste |
| 2014/0101876 A1 | 4/2014 | Rogers et al. |
| 2014/0155868 A1 | 6/2014 | Nelson et al. |
| 2014/0227144 A1 | 8/2014 | Liu et al. |
| 2014/0228775 A1 | 8/2014 | Burkholz et al. |
| 2014/0243797 A1 | 8/2014 | Jensen et al. |
| 2014/0336610 A1 | 11/2014 | Michel et al. |
| 2015/0086441 A1 | 3/2015 | She et al. |
| 2015/0141934 A1 | 5/2015 | Gardner et al. |
| 2015/0148287 A1 | 5/2015 | Woo et al. |
| 2015/0217106 A1 | 8/2015 | Banik et al. |
| 2015/0258324 A1 | 9/2015 | Chida et al. |
| 2015/0298893 A1 | 10/2015 | Welp |
| 2015/0306367 A1 | 10/2015 | DiFiore |
| 2015/0314119 A1 | 11/2015 | Anderson et al. |
| 2015/0320992 A1 | 11/2015 | Bonnet et al. |
| 2015/0343174 A1 | 12/2015 | Ziebol et al. |
| 2016/0001056 A1 | 1/2016 | Nelson et al. |
| 2016/0001058 A1 | 1/2016 | Ziebol et al. |
| 2016/0015863 A1 | 1/2016 | Gupta et al. |
| 2016/0045629 A1 | 2/2016 | Gardner et al. |
| 2016/0088995 A1 | 3/2016 | Ueda et al. |
| 2016/0089530 A1 | 3/2016 | Sathe |
| 2016/0101223 A1 | 4/2016 | Kelley, III et al. |
| 2016/0101276 A1 | 4/2016 | Tekeste |
| 2016/0106969 A1 | 4/2016 | Neftel |
| 2016/0158521 A1 | 6/2016 | Hoang et al. |
| 2016/0158522 A1 | 6/2016 | Hoang et al. |
| 2016/0213912 A1 | 7/2016 | Daneluzzi |
| 2016/0250420 A1 | 9/2016 | Maritan et al. |
| 2016/0354596 A1 | 12/2016 | DiFiore |
| 2017/0020911 A1 | 1/2017 | Berry et al. |
| 2017/0042636 A1 | 2/2017 | Young |
| 2017/0143447 A1 | 5/2017 | Rogers et al. |
| 2017/0182241 A1 | 6/2017 | DiFiore |
| 2017/0203092 A1 | 7/2017 | Ryan et al. |
| 2017/0239443 A1 | 8/2017 | Abitabilo et al. |
| 2018/0028403 A1 | 2/2018 | Fangrow |
| 2018/0214684 A1 | 8/2018 | Avula et al. |
| 2019/0351211 A1* | 11/2019 | Dombrowski ........ A61M 39/16 |
| 2020/0139037 A1 | 5/2020 | Ziebol et al. |
| 2020/0139102 A1 | 5/2020 | Ziebol et al. |
| 2020/0324102 A1 | 10/2020 | Fangrow |
| 2020/0406020 A1 | 12/2020 | Fangrow |
| 2021/0106805 A1 | 4/2021 | Fangrow |

(56) References Cited

U.S. PATENT DOCUMENTS

| | | | |
|---|---|---|---|
| 2021/0162194 | A1 | 6/2021 | Gardner |
| 2021/0205596 | A1 | 7/2021 | Ziebol et al. |
| 2021/0308442 | A1 | 10/2021 | Gardner |
| 2022/0226629 | A1 | 7/2022 | Ziebel |
| 2022/0288258 | A1 | 9/2022 | Gardner |
| 2022/0288376 | A1 | 9/2022 | Ziebol |
| 2022/0313977 | A1* | 10/2022 | Gugel .................. A61M 5/1411 |
| 2022/0379035 | A1 | 12/2022 | Anderson |
| 2022/0387685 | A1 | 12/2022 | Ziebol |
| 2022/0401652 | A1 | 12/2022 | Anderson |
| 2023/0069367 | A1 | 3/2023 | Ziebol |
| 2023/0105566 | A1 | 4/2023 | Fangrow |
| 2023/0121450 | A1 | 4/2023 | Ziebol |

FOREIGN PATENT DOCUMENTS

| | | |
|---|---|---|
| CA | 2 841 832 | 6/2019 |
| CN | 2402327 Y | 10/2000 |
| CN | 2815392 Y | 9/2006 |
| CN | 201150420 Y | 11/2008 |
| CN | 101405042 | 4/2009 |
| CN | 201519335 U | 7/2010 |
| CN | 102202716 | 9/2011 |
| CN | 102 844 073 A | 12/2012 |
| CN | 103796704 | 12/2016 |
| CN | 106902402 | 6/2017 |
| CN | 106902405 | 6/2017 |
| CN | 107837428 | 3/2018 |
| DE | 3515665 | 5/1986 |
| DE | 89 06 628 U1 | 9/1989 |
| DE | 43 34 272 | 4/1995 |
| DE | 29617133 | 1/1997 |
| DE | 102007025900 | 12/2008 |
| EP | 0 088 341 | 9/1983 |
| EP | 0 108 785 | 5/1984 |
| EP | 0 174 162 | 3/1986 |
| EP | 0 227 219 | 7/1987 |
| EP | 0 237 239 | 9/1987 |
| EP | 0 245 872 | 11/1987 |
| EP | 0 257 485 | 3/1988 |
| EP | 0 639 385 | 2/1995 |
| EP | 0 734 721 | 10/1996 |
| EP | 0 769 265 | 4/1997 |
| EP | 1 061 000 | 10/2000 |
| EP | 1 331 020 | 7/2003 |
| EP | 1 471 011 | 10/2004 |
| EP | 1 442 753 | 2/2007 |
| EP | 1 813 293 | 8/2007 |
| EP | 1 977 714 | 10/2008 |
| EP | 1 312 008 | 4/2009 |
| EP | 2 444 117 | 4/2012 |
| EP | 2 606 930 | 6/2013 |
| EP | 2 671 604 | 12/2013 |
| EP | 2 731 658 | 5/2014 |
| FR | 2 493 149 A | 5/1982 |
| FR | 2 506 162 | 11/1982 |
| FR | 2 782 910 | 3/2000 |
| GB | 123221 | 2/1919 |
| GB | 2 296 182 | 6/1996 |
| GB | 2 333 097 | 7/1999 |
| GB | 2 387 772 | 10/2003 |
| JP | 57-131462 U | 8/1982 |
| JP | 04-99950 | 2/1992 |
| JP | 05-31180 A | 2/1993 |
| JP | 09-216661 A | 8/1997 |
| JP | 2000-157630 A | 6/2000 |
| JP | 2002-210011 A | 7/2002 |
| JP | 2002-234567 A | 8/2002 |
| JP | 2002-291906 | 10/2002 |
| JP | 2005-218649 | 8/2005 |
| JP | 2006-182663 A | 7/2006 |
| JP | 2006-223583 A | 8/2006 |
| JP | 2009-006148 A | 1/2009 |
| JP | 2009-544450 A | 12/2009 |
| JP | 2011-036691 | 2/2011 |
| JP | 2011-528647 | 11/2011 |
| JP | 2012-020125 A | 2/2012 |
| JP | 2013-520287 | 6/2013 |
| JP | 2014-117461 | 6/2014 |
| JP | 2014-533593 A | 12/2014 |
| JP | 2015-526195 A | 9/2015 |
| JP | 2016-506856 A | 3/2016 |
| JP | 2017-515553 A | 6/2017 |
| RU | 2 246 321 C1 | 2/2005 |
| WO | WO 83/03975 | 11/1983 |
| WO | WO 85/05040 | 11/1985 |
| WO | WO 93/20806 | 10/1993 |
| WO | WO 95/07691 | 3/1995 |
| WO | WO 96/35416 | 11/1996 |
| WO | WO 96/38136 | 12/1996 |
| WO | WO 97/19701 | 6/1997 |
| WO | WO 98/12125 | 3/1998 |
| WO | WO 98/48872 | 11/1998 |
| WO | WO 99/44665 | 9/1999 |
| WO | WO 2001/70199 A1 | 9/2001 |
| WO | WO 2002/05188 | 1/2002 |
| WO | WO 2002/47581 | 6/2002 |
| WO | WO 2002/49544 | 6/2002 |
| WO | WO 2003/015677 | 2/2003 |
| WO | WO 2003/070296 | 8/2003 |
| WO | WO 2004/035129 | 4/2004 |
| WO | WO 2004/112846 | 12/2004 |
| WO | WO 2005/112954 | 12/2005 |
| WO | WO 2005/112974 | 12/2005 |
| WO | WO 2006/007690 | 1/2006 |
| WO | WO 2006/044236 | 4/2006 |
| WO | WO 2006/102756 | 10/2006 |
| WO | WO 2007/008511 | 1/2007 |
| WO | WO 2007/056773 | 5/2007 |
| WO | WO 2007/137056 | 11/2007 |
| WO | WO 2008/014437 | 1/2008 |
| WO | WO 2008/042285 | 4/2008 |
| WO | WO 2008/086631 | 7/2008 |
| WO | WO 2008/089196 | 7/2008 |
| WO | WO 2008/100950 | 8/2008 |
| WO | WO 2008/140807 | 11/2008 |
| WO | WO 2009/002474 | 12/2008 |
| WO | WO 2009/060322 | 5/2009 |
| WO | WO 2009/117135 | 9/2009 |
| WO | WO 2009/123709 | 10/2009 |
| WO | WO 2009/136957 | 11/2009 |
| WO | WO 2009/153224 | 12/2009 |
| WO | WO 2010/002757 | 1/2010 |
| WO | WO 2010/002808 | 1/2010 |
| WO | WO 2010/011616 | 1/2010 |
| WO | WO 2010/034470 | 4/2010 |
| WO | WO 2010/039171 | 4/2010 |
| WO | WO 2010/062589 | 6/2010 |
| WO | WO 2011/012379 | 2/2011 |
| WO | WO 2011/028722 | 3/2011 |
| WO | WO 2011/053924 | 5/2011 |
| WO | WO 2011/106374 | 9/2011 |
| WO | WO 2011/119021 | 9/2011 |
| WO | WO 2012/118829 | 9/2012 |
| WO | WO 2012/162006 | 11/2012 |
| WO | WO 2013/009998 | 1/2013 |
| WO | WO 2013/023146 | 2/2013 |
| WO | WO 2013/082180 | 6/2013 |
| WO | WO 2013/184716 | 12/2013 |
| WO | WO 2013/192574 | 12/2013 |
| WO | WO 2014/031628 | 2/2014 |
| WO | WO 2014/074929 | 5/2014 |
| WO | WO 2014/126867 | 8/2014 |
| WO | WO 2014/140949 | 9/2014 |
| WO | WO 2014/159346 | 10/2014 |
| WO | WO 2015/074087 | 5/2015 |
| WO | WO 2015/119940 | 8/2015 |
| WO | WO 2015/120336 | 8/2015 |
| WO | WO 2015/164129 | 10/2015 |
| WO | WO 2015/164134 | 10/2015 |
| WO | WO 2015/168677 | 11/2015 |
| WO | WO 2015/174953 | 11/2015 |
| WO | WO 2016/025775 | 2/2016 |
| WO | WO 2016/182822 | 11/2016 |

(56) References Cited

FOREIGN PATENT DOCUMENTS

| | | |
|---|---|---|
| WO | WO 2017/015047 | 1/2017 |
| WO | WO 2017/127364 | 7/2017 |
| WO | WO 2017/127365 | 7/2017 |
| WO | WO 2018/009653 | 1/2018 |
| WO | WO 2018/071717 | 4/2018 |
| WO | WO 2018/204206 | 11/2018 |
| WO | WO 2018/237090 | 12/2018 |
| WO | WO 2018/237122 | 12/2018 |
| WO | WO 2019/178560 | 9/2019 |
| WO | WO 2019/246472 | 12/2019 |
| WO | WO 2020/097366 | 5/2020 |
| WO | WO 2020/251947 | 12/2020 |
| WO | WO 2022/125474 | 6/2022 |

OTHER PUBLICATIONS

Otto, Mosby's Pocket Guide to Infusion Therapy. Elsevier Health Sciences, 2004. pp. 65-66. Accessed at: http://books.google.com/books?id=j8T14HwWdS4C&lpg=PP1&pg=PP1#v=onepage&f=false (Year: 2004).
"Small-bore connectors for liquids and gases in healthcare applications—Part : Connectors for intravascular or hypodermic applications," ISO 80369-7, Corrected version dated Dec. 1, 2016 (50 pages).
Hospira, "You Work in Neverland," Lifeshield Product Brochure in 2 pages, Published 2009.
Baxter Minicap: Photographs of the Baxter Minicap (Sep. 1, 1998) (4 pages).
Baxter, "Peritoneal Dialysis Patient Connectology," Product Descriptions in 1 page, downloaded Jul. 1, 2011.
Beta Cap II Advertisement from Quinton Instrument Co. (Aug. 1981).
Catheter Connections, "Introducing DualCap," Product Brochure in 1 page, Copyright 2011.
Charney, "Baxter Healthcare InterlinkTM IV Access System" in 1 page, from Handbook of Modern Hospital Safety. Published Mar. 1999.
Clave® Needlefree Connector, icumedial, human connections, 2 page brochure. 2012, M1-1065 Rev. 04.
Conical Fittings: International Standard, "Conical fittings with 6% (Luer) Taper for Syringes, Needles and certain Other Medical Equipment—Part 2: Lock Fittings", Ref. No. ISO 594-2:1998. International Organization for Standardization (Sep. 1, 1998) 2nd ed. (16 pages).
Devine, redacted version of letter from David A. Divine, Esq. of Lee & Hayes, dated May 16, 2011 (3 pages).
Devine, redacted version of letter from David A. Divine, Esq. of Lee & Hayes, dated May 27, 2011 (3 pages).
Du. Y, et al. Protein adsorption on polyurethane catheters modified with a novel antithrombin-heparin covalent complex, Journal of Biomedical Materials Research Part A, 2006, 216-225.
Holmer, E. et al. The molecular-weight dependence of the rate-enhancing effect of heparin on the inhibition of thrombin, Factor Xa, Factor IXa, Factor XIa, Factor XIIa and kallikrein by antithrombin, Biochem. J. (1981) 193, 395-400.
Hyprotek, "Port Protek," Product Brochure in 1 page, downloaded Sep. 19, 2011 from http://www.hyprotek.com/products.html.
ICU Medical Antimicrobial Microclave, first sold Jan. 21, 2010, p. 1-2.
Klement, P. et al. Chronic performance of polyurethane catheters covalently coated with ATH complex: A rabbit jugular vein model, Biomaterials, (2006), 27, 5107-5117.
Menyhay et al., "Disinfection of Needleless Catheter Connectors and Access Ports with Alcohol May Not Prevent Microbial Entry: The Promise of a Novel Antiseptic-Barrier Cap" Infection Control Hospital and Epidemiology, vol. 27, No. 1 (Jan. 2006) (5 pages).
Photographs of the Baxter Minicap (Sep. 1, 1998) (4 pages).
V-Link Luer Activated Device, with VitalShield Protective Coating, 2 page brochure, Baxter Dec. 2009.
U.S. Appl. No. 16/882,210, filed May 22, 2020.
Value Plastics, Inc., "Finger Snap Luer Lock Ring (FSLLR)," drawn by Frank Lombardi, May 29, 2011.
International Search Report and Written Opinion, re PCT Application No. PCT/US2021/062079, dated Apr. 7, 2022.
US, U.S. Pat. No. 9,022,984, Oct. 26, 2009, Apparatus for Delivery of Device and Antimicrobial Agent Into Trans-Dermal Catheter.
US, U.S. Pat. No. 9,072,868, Oct. 26, 2009, Device for Delivery of Antimicrobial Agent Into Trans-Dermal Catheter.
US, U.S. Pat. No. 9,849,276, Jul. 12, 2012, Method of Delivering Antimicrobial to a Catheter.
US, U.S. Pat. No. 11,389,634, Dec. 21, 2017, Device for Delivery of Antimicrobial Agent Into Trans-Dermal Catheter.
US, U.S. Appl. No. 17/710,887, filed Mar. 31, 2022, Device for Delivery of Antimicrobial Agent Into a Medical Device.
US, U.S. Pat. No. 8,622,995, Jan. 28, 2013, Method for Delivery of Antimicrobial to Proximal End of Catheter.
US, U.S. Pat. No. 8,622,996, Mar. 15, 2013, Method for Applying Antimicrobial to Proximal End of Catheter.
US, U.S. Pat. No. 9,352,142, May 22, 2015, Method for Coating a Catheter With an Antimicrobial Agent.
US, U.S. Pat. No. 10,159,829, Jul. 7, 2015, Packaging Container for Antimicrobial Caps.
US, U.S. Pat. No. 11,351,353, Dec. 20, 2018, Packaging Container for Antimicrobial Caps.
US, U.S. Appl. No. 17/832,277, filed Jun. 3, 2022, Method of Coating a Transdermal Catheter With an Antimicrobial Agent.
US, U.S. Pat. No. 9,078,992, Jun. 11, 2013, Medical Device for Applying Antimicrobial to Proximal End of Catheter.
US, U.S. Pat. No. 11,433,215, Nov. 21, 2019, Antimicrobial Device Comprising a Cap With Ring and Insert.
US, U.S. Appl. No. 17/891,990, filed Aug. 19, 2022, Antimicrobial Device Comprising a Cap With Ring and Insert.
US, U.S. Pat. No. 10,525,250, May 6, 2019, Infusion Device With Antimicrobial Properties.
US, U.S. Pat. No. 11,534,595, Jun. 18, 2019, Device for Delivering an Antimicrobial Composition Into an Infusion Device.
US, U.S. Pat. No. 11,541,220, Jun. 20, 2019, Needleless Connector With Antimicrobial Properties.
US, U.S. Pat. No. 11,541,221, Jun. 21, 2019, Tubing Set With Antimicrobial Properties.
US, U.S. Pat. No. 11,400,195, Aug. 28, 2019, Peritoneal Dialysis Transfer Set With Antimicrobial Properties.
US, U.S. Appl. No. 17/843,908, filed Jun. 17, 2022, Medical Device With Antimicrobial Properties.
US, U.S. Appl. No. 16/558,921, filed Sep. 3, 2019, Syringe With Antimicrobial Properties.
US, U.S. Appl. No. 18/061,385, filed Dec. 2, 2022, Device for Delivering an Antimicrobial Composition Into a Medical Device.
US, U.S. Appl. No. 17/143,082, filed Jan. 6, 2021, Antimicrobial Cap for Luer Connector.
US, U.S. Pat. No. 10,524,982, Oct. 6, 2017, Medical Connectors Configured to Receive Emitters of Therapeutic Agents.
US, U.S. Pat. No. 11,559,467, Nov. 25, 2019, Medical Connectors Configured to Receive Emitters of Therapeutic Agents.
US, U.S. Appl. No. 18/066,670, filed Dec. 15, 2022, Medical Connectors Configured to Receive Emitters of Therapeutic Agents.
US, U.S. Appl. No. 16/717,199, filed Dec. 17, 2019, Priming Cap.
US, U.S. Pat. No. 10,744,316, Apr. 8, 2019, Sanitizing Caps for Medical Connectors.
US, U.S. Pat. No. 11,497,904, Jul. 1, 2020, Sanitizing Caps for Medical Connectors.
US, U.S. Appl. No. 17/937,541, filed Oct. 3, 2022, Sanitizing Caps for Medical Connectors.
US, U.S. Pat. No. 11,517,733, Oct. 30, 2019, Medical Fluid Connectors and Methods for Providing Additives in Medical Fluid Lines.
US, U.S. Appl. No. 17/021,226, filed Sep. 15, 2020, Sanitizing Caps for Medical Connectors.
US, U.S. Pat. No. 8,167,847, Dec. 17, 2020, System for Sterilizing Intravenous Connectors and Tubing.
US, U.S. Pat. No. 8,167,847, Jun. 22, 2007, Antiseptic Cap and Antiseptic Cap Equipped Plunger and Syringe Barrel Assembly.
US, U.S. Pat. No. 8,968,268, Apr. 26, 2012, Antiseptic Cap.

(56) References Cited

OTHER PUBLICATIONS

US, U.S. Pat. No. 9,707,349, Oct. 11, 2012, Antiseptic Cap.
US, U.S. Pat. No. 9,707,348, Jun. 19, 2008, Antiseptic Cap With Thread Cover.
US, U.S. Pat. No. 8,231,602, Apr. 27, 2011, Method of Cleaning and Covering an Access Site.
US, U.S. Pat. No. 8,845,593, May 16, 2012, Antiseptic Cap With Antiseptic.
US, U.S. Pat. No. 9,700,676, Jul. 27, 2012, Method of Cleaning and Covering an Access Site.
US, U.S. Pat. No. 9,700,677, Sep. 29, 2014, Antiseptic Cap With Antiseptic.
US, U.S. Pat. No. 9,700,710, Nov. 3, 2011, Antiseptic Cap Equipped Syringe.
US, U.S. Pat. No. 9,259,535, Jul. 12, 2012, Antiseptic Cap Equipped Syringe.
US, U.S. Pat. No. 9,707,350, Jul. 14, 2015, Antiseptic Cap Equipped Syringe.
US, U.S. Pat. No. 10,328,207, Jun. 29, 2017, Antiseptic Cap.
US, U.S. Pat. No. 11,229,746, May 21, 2019, Antiseptic Cap.
US, U.S. Pat. No. 11,160,932, Dec. 11, 2020, Antiseptic Cap That Releases a Gas Such as Nitric Oxide.
US, U.S. Appl. No. 17/576,842, filed Jan. 14, 2022, Antiseptic Cap That Releases a Gas Such as Nitric Oxide.
US, U.S. Appl. No. 17/822,074, filed Aug. 24, 2022, Antiseptic Cap That Releases a Gas Such as Nitric Oxide.
U.S. Pat. No. 10,016,587, May 21, 2012, Caps for Needleless Connectors.
U.S. Pat. No. 10,695,550, Jun. 25, 2018, Caps for Needleless Connectors.
U.S. Appl. No. 16/882,210, filed May 22, 2020, Caps for Needleless Connectors.
US, U.S. Pat. No. 9,867,975, May 23, 2011, Antiseptic Line Cap.
US, U.S. Pat. No. 10,166,381, Mar. 14, 2013, Antiseptic Cap.
US, U.S. Pat. No. 10,806,919, Oct. 16, 2018, Antiseptic Cap.
US, U.S. Appl. No. 17/025,201, filed Sep. 18, 2020, Antiseptic Cap.
US, U.S. Appl. No. 13/968,151, filed Aug. 15, 2013, Disinfecting Mouth Guard for Vap Prevention.
US, U.S. Appl. No. 14/547,125, filed Nov. 18, 2014, Medicant Injection Device.
US, U.S. Appl. No. 14/554,018, filed Nov. 25, 2014, Catheter Lock Solution Formulations.
US, U.S. Appl. No. 14/616,593, filed Feb. 6, 2015, Swab Devices.
US, U.S. Pat. No. 10,046,156, May 4, 2015, Strip Package for Antiseptic Cap.
US, U.S. Pat. No. 10,821,278, Aug. 13, 2018, Strip Package for Antiseptic Cap.
US, U.S. Appl. No. 17/085,197, filed Oct. 30, 2020, Strip Package for Antiseptic Cap.
US, U.S. Appl. No. 14/826,180, filed Aug. 13, 2015, Disinfectant Caps.
US, U.S. Appl. No. 17/830,183, filed Jun. 1, 2022, Caps to Provide a Physical Barrier to an Access Site of a Medical Connector.
ICU Medical SwabPack, top-access bag of disinfecting caps for needlefree connectors, on sale at least as early as Jan. 2012.
Thread Check Inc., ISO 80369-7 replaces ISO 594-2:1998€, retrieved 2023; ISO 80369-7 published Oct. 2016, https://www.threadcheck.com/isl-80369/technicalinfo#gref (Year: 2016).
International Preliminary Report on Patentability, re PCT/US15/14921, dated Jun. 13, 2023.

* cited by examiner

PROXIMAL DIRECTION ← → DISTAL DIRECTION

SECTION L-L

SECTION K-K

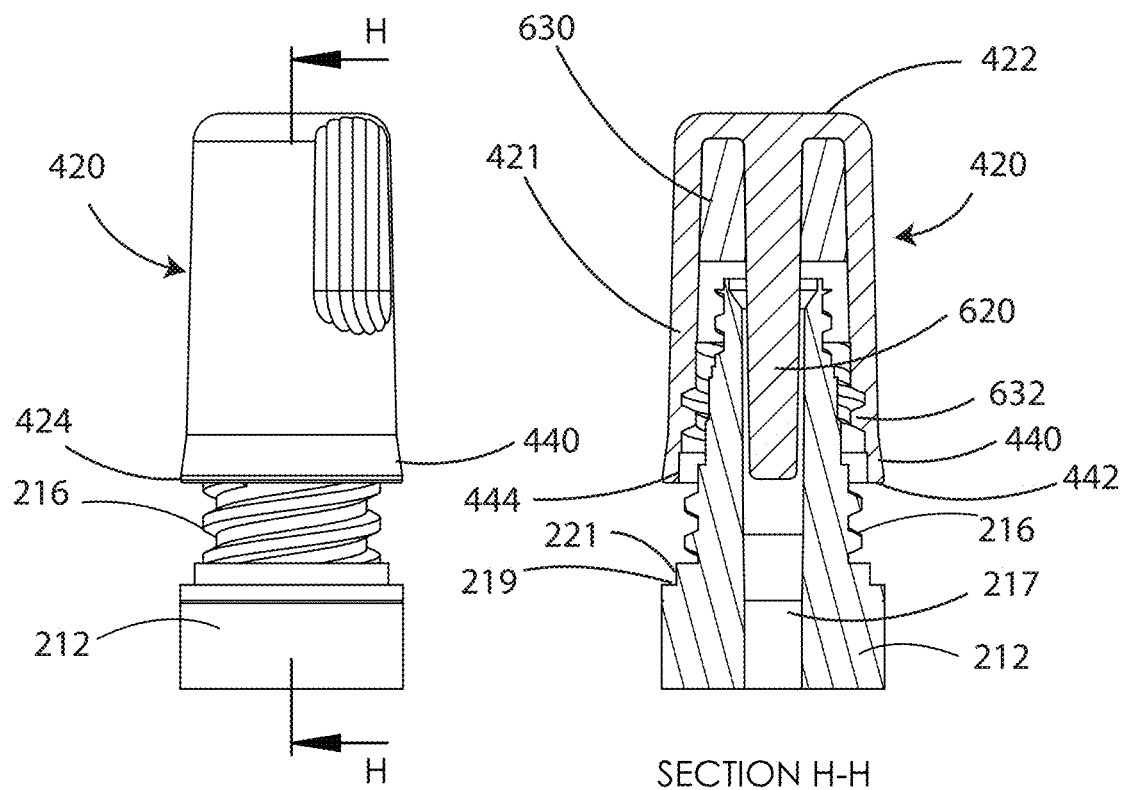

PERITONEAL DIALYSIS CAPS, SYSTEMS AND METHODS

PRIORITY CLAIM AND INCORPORATION BY REFERENCE

The present application claims the benefit under 35 U.S.C. § 119(e) to U.S. Patent Application No. 63/122,470, filed on Dec. 7, 2020, the contents of which is hereby incorporated by reference herein in their entirety as if fully set forth herein for all purposes. Any and all applications for which a foreign or domestic priority claim is identified in the Application Data Sheet as filed with the present application are hereby incorporated by reference herein in their entirety and made a part of this specification.

FIELD

Embodiments disclosed herein relate to peritoneal dialysis devices and methods, including peritoneal dialysis caps, cap systems for use during peritoneal dialysis, and methods for administering antimicrobial substances to peritoneal dialysis devices.

BACKGROUND

Infusion devices, such as catheters and on-catheter devices, are commonly used in providing modern medical care to patients. For example, catheters such as hemodialysis catheters, peritoneal dialysis catheters, peripherally inserted central catheters, midline catheters, and drainage catheters are all commonly used in providing modern medical care to patients. Other infusion devices used in providing medical care include needleless connectors, intravenous (IV) administration sets, peritoneal dialysis lines, transfer sets, syringes, valves and filters.

These infusion devices are useful for treating various medical conditions. For example, peritoneal catheters allow patients with renal disease to have waste and fluid removed from their bodies. Thus, catheters and other infusion devices make critical medical care possible and are often essential to providing improved health care outcomes.

However, long-term use of catheters has a serious drawback in that a significant percentage of catheters fail due to infection, resulting in elevated mortality rates and significantly increased healthcare costs associated with treatment. Furthermore, infections are a leading cause of death in the United States, and many of those infections are attributable to infusion devices. The mortality rate associated with such infections is considerable. Therefore, a need exists for a solution to reduce infections relating from the use of infusion devices.

SUMMARY OF SOME EXEMPLIFYING EMBODIMENTS

The systems, methods, and devices of this disclosure each have several innovative aspects, implementations, or aspects, no single one of which is solely responsible for the desirable attributes disclosed herein. Nothing in this specification is essential or indispensable. Any structure, material, component, method, or step described and/or illustrated in any embodiment in this specification can be provided by itself and/or combined with any other structure, material, component, method, or step described and/or illustrated in any other embodiment in this specification or known in the art. All relative sizes and dimensions of parts and components illustrated in the drawings are intended to form part of this disclosure but should not be used to limit the scope of any claim unless recited in such claim. Any words in this specification that are generally associated with circles or circular structures, such as the words radius, radial, diameter, or circumference, should be understood to also apply to non-circular structures in analogous ways, such as denoting cross-sectional widths or perimeters.

Infection-causing organisms are ever present in the environment; they live on patients' skin and can survive and be transmitted in air and water. Conventional medical device connectors and caps, such as male and female connectors with tapered luers, have a threaded region along with a tapered sealing region, such as an overlapping sealing region of the tapered portions of male and female connectors. The overlapping sealing regions seal fluid inside the medical device and keep air and organisms out. However, our testing shows that organisms can still migrate through the threaded region and penetrate a portion of the way into the sealing region. This results in organisms being present along the walls of portions of the devices. When the male and female connectors are separated from one another, some organisms can remain on the walls of the male and female connectors. The next time a connection is made, some of the organisms can be pushed past the sealing surface and into the fluid path. Once organisms are in the fluid path they can multiply, spread, and cause an infection. Peritoneal dialysis transfer sets can be used to make fluid connections between a peritoneal dialysis catheter and a patient line, for instilling and removing dialysate from the peritoneal cavity.

Disclosed herein are embodiments of a cap for a medical connector that can include a body having a closed proximal end and an open distal end, an interior volume within the body, an elongate member comprising an antimicrobial extending from the proximal end of body axially through at least a portion of the interior volume, the elongate member, threads for securing the cap to a medical connector, and a radially inwardly facing sealing surface on the cap, the inwardly facing sealing surface located distal to the threads and providing a seal, such as a liquid-tight and/or an air-tight seal, between the cap and the medical connector when the cap is installed on the medical connector.

Any embodiments of the caps, methods, and systems disclosed herein can include, in additional embodiments, one or more of the following steps, features, components, and/or details, in any combination with any of the other steps, features, components, and/or details of any other embodiments disclosed herein: wherein the medical connector is part of a peritoneal dialysis transfer set; wherein the radially inwardly facing sealing surface on the cap provides a seal (e.g., air-tight and/or liquid-tight) between the cap and the medical connector when the cap is installed on the medical connector by constricting around an outer surface of the medical connector; further comprising a distally facing sealing surface on the cap, wherein the distally facing sealing surface is located distal to the threads, and the distally facing sealing surface provides a second liquid-tight seal between the cap and the medical connector when the cap is installed on the medical connector; wherein the distally facing sealing surface is located at a distal end of the cap and has a generally planar surface that is approximately perpendicular to a longitudinally axial centerline of the cap; wherein all sealing surfaces are located in a distal portion of the body of the cap; wherein the cap is configured to overlap a portion of an outer surface of the medical connector and to create a seal against the portion of the outer surface of the medical connector that is overlapped; comprising a porous element in the interior volume within the body, the porous element being dry and being free of any antimicrobial substances prior to installation on a medical connector; wherein the porous element is configured to retain a fluid exiting the medical connector upon installation of the cap on the transfer set; wherein the porous element encloses a volume of at least about 75%, or less than or equal to about 75%, or between about 75% to about 125%, or approximately 125%, or less than or equal to about 125%, or at least about 125%, of a volume of liquid that can be displaced by the elongate member as the elongate member is advanced into the medical connector; wherein the porous element is sized and configured to contact an end of the medical connector when the cap is engaged with the medical connector; wherein the elongate member does not form a fluid seal within a lumen of the medical connector; and/or wherein the antimicrobial comprises chlorhexidine acetate. Also disclosed herein are embodiments of a kit that can include a cap for a medical connector of any embodiments disclosed herein and a base element, wherein the cap is coupled with the base element.

Disclosed herein are embodiments of a cap for a medical connector that can include a body having a closed proximal end and an open distal end, an interior volume within the body, an elongate member extending from the proximal end of body axially through at least a portion of the interior volume, the elongate member comprising a dry antimicrobial on a surface thereof, threads for securing the cap to a medical connector, a porous element in the interior volume within the body, wherein the porous element is not saturated with or substantially free of an antimicrobial before use, and a radially inwardly facing sealing surface on the cap. In some embodiments, the inwardly facing sealing surface can be located distal to the threads and can provide a liquid-tight seal between the cap and the medical connector when the cap is installed on the medical connector. In some embodiments, the porous element can be at least about 95% free of an antimicrobial before use. This can mean that the porous element can have about 5% or less of a total amount of an antimicrobial that the porous element can be capable of retaining within the porous element. In some embodiments, the porous element can be at least about 90% free of an antimicrobial before use. This can mean means that the porous element can have 10% or less of a total amount of an antimicrobial that the porous element can support.

Also disclosed herein are embodiments of a method of delivering an antimicrobial to a medical connector that can include advancing a cap into engagement with a medical connector having a lumen having an inner wall, an outer wall having an exterior surface, and a proximal end face, advancing an elongate member of the cap into the lumen so as to wet a dry antimicrobial coated on an outside surface of the elongate member to dissolve the antimicrobial into a liquid within the medical connector, and sealing the cap against an outwardly facing surface of the medical connector with a sealing surface located at a distal end of the cap.

Disclosed herein are embodiments of a cap or set of caps (collectively referred to herein as a cap) for a medical connector for peritoneal dialysis that can include a partially enclosed interior space (also referred to herein as an interior space), an elongate member positioned at least partially within the partially enclosed interior space, an antimicrobial on or in the elongate member, threads on the cap for securing the cap to the medical connector, and a sealing surface on the cap. In some embodiments, the sealing surface can be located distal to the threads and can provide a liquid-tight seal between the cap and the medical connector when the cap is installed on the medical connector.

Disclosed herein are embodiments of a cap for a medical connector for peritoneal dialysis that can include a partially enclosed interior space, an elongate member positioned at least partially within the partially enclosed interior space, an antimicrobial on or in the elongate member, threads on the cap for securing the cap to the medical connector, and a sealing surface on the cap. In some embodiments, the sealing surface can be located distal to the threads and can provide a first sealing capacity when installed on the medical connector. The first sealing capacity can be more than 50 percent of a total sealing capacity between the cap and the medical connector when the cap is installed on the medical connector.

Disclosed herein are embodiments of a cap for a medical connector for peritoneal dialysis that can include a partially enclosed interior space, an elongate member positioned at least partially within the partially enclosed interior space, an antimicrobial on or in the elongate member, threads on the cap for securing the cap to the medical connector, and a sealing surface on the cap. In some embodiments, the sealing surface can have an inner diameter that is greater than an inner diameter of the threads on the cap.

Disclosed herein are embodiments of a cap for a medical connector for peritoneal dialysis that can include an elongate member, an antimicrobial on or in the elongate member, threads on the cap for securing the cap to the medical connector, the threads on the cap having an inner diameter, and a sealing surface on the cap, the sealing surface having an inner diameter greater than the inner diameter of the threads on the cap.

Disclosed herein are embodiments of a cap for a medical connector for peritoneal dialysis that can include a partially enclosed interior space, an elongate member positioned at least partially within the partially enclosed interior space, an antimicrobial on or in the elongate member, threads on the cap for securing the cap to the medical connector, and a sealing surface on the cap. In some embodiments, the sealing surface can be located distal to the threads and can be configured to provide a seal between the cap and the medical connector. In some embodiments, the cap can be configured to not form an additional seal with the medical connector when installed on the medical connector.

Disclosed herein are embodiments of a cap for delivering an antimicrobial to a medical connector that can include an elongate member, an antimicrobial on or in the elongate member, threads having an inner diameter, and a sealing surface. The threads can be configured to secure the cap to the medical connector, and the sealing surface can have an inner diameter greater than the inner diameter of the threads.

Disclosed herein are embodiments of a cap for delivering an antimicrobial to a medical connector that can include an elongate member, an antimicrobial on or in the elongate member, threads configured to secure the cap to the medical connector, and a sealing surface, wherein the elongate member is located at least partially proximal to the sealing surface.

Disclosed herein are embodiments of a cap for a medical connector that can include a partially enclosed interior space, an elongate member at least partially within the partially enclosed interior space, an antimicrobial on or in the elongate member, and a compressible porous element (also referred to herein as a porous material) positioned near a proximal portion of the elongate member, the compressible porous element substantially free of an antimicrobial before use.

Disclosed herein are embodiments of a cap for a medical connector that can include a proximal end and a distal end, with an opening on the distal end leading to an interior of the cap, treads located in a partially enclosed interior space of the cap, an elongate member at least partially within the partially enclosed interior space of the cap, a dry antimicrobial on the elongate member, and a sealing surface located entirely distal to threads on the cap.

Disclosed herein are embodiments of a cap for a medical connector that can include an elongate member configured to be inserted into a lumen of the medical connector, an antimicrobial on or in the elongate member, and a sealing surface located distal to at least a portion of the elongate member and configured to form a fluid tight seal.

Disclosed herein are embodiments of a cap for a medical connector that can include an elongate member configured to be inserted into a lumen of the medical connector, an antimicrobial on or in the elongate member, and a sealing surface configured to form a fluid tight seal on an outer surface of the medical connector.

Disclosed herein are embodiments of a cap for a medical connector that can include an elongate member configured to be inserted into a lumen of the medical connector, an antimicrobial on or in the elongate member, and a sealing surface having an internal diameter that is larger than a thread outer diameter of the medical connector.

Disclosed herein are embodiments of a cap for a medical connector that can include a proximal end and a distal end, with an opening on the distal end, an elongate member at least partially within an interior of the cap, a dry antimicrobial on the elongate member, and a sealing surface on the distal end of the cap, wherein the sealing surface is configured to prevent venting after the cap is installed.

Disclosed herein are embodiments of a cap for a medical connector that can include a proximal end and a distal end, with an opening on the distal end, an elongate member at least partially within an interior of the cap, a dry antimicrobial on the elongate member, and a porous element positioned at a proximal end of the elongate member, wherein, after installation of the cap onto the medical connector, the dry antimicrobial can be configured to move within a lumen region between the porous element and a clamp of the medical device.

Disclosed herein are embodiments of a method of in-situ formation of an antimicrobial porous element including providing a cap having a proximal end and a distal end, an opening on the distal end, an elongate member at least partially within an interior of the cap, a dry antimicrobial on the elongate member, and a compressible porous element substantially free of antimicrobial, providing a medical device having a lumen, and inserting the elongate member into a liquid contained within the lumen of the medical device such that the dry antimicrobial dissolves into the liquid to create an antimicrobial liquid and wets the porous element with the antimicrobial liquid.

Disclosed herein are embodiments of a method of in-situ formation of an antimicrobial porous element that can include providing a cap having: a proximal end and a distal end, an opening on the distal end, an elongate member at least partially within an interior of the cap, the elongate member having a volume, a dry antimicrobial on the elongate member, and a compressible porous element partially surrounding a portion of the elongate member, and inserting the elongate member into a liquid such that the volume of the elongate member displaces a portion of the liquid through the compressible porous element and at least a portion of the dry antimicrobial dissolves into the liquid to form an antimicrobial liquid, and at least a portion of the antimicrobial liquid makes contact with the porous element. In some embodiments, the compressible porous element can be substantially free of antimicrobial and can at least partially contain air.

Disclosed herein are embodiments of a method of cleaning a proximal end of a dialysis transfer set that can include providing a cap having a proximal end and a distal end, with an opening on the distal end, an elongate member at least partially within the interior of the cap, a dry antimicrobial on the elongate member, and a compressible porous element partially surrounding a portion of the elongate member, and installing the cap on the transfer set. In some embodiments, the compressible porous element can be compressed during installation by a swiping motion on the proximal end of the transfer set.

Disclosed herein are embodiments of a method of installing a cap to a medical connector that can include providing a cap having a proximal end and a distal end, an opening on the distal end, an elongate member at least partially within the interior of the cap, a dry antimicrobial on the elongate member, a dry compressible porous element partially surrounding a portion of the elongate member, and installing the cap on the transfer set. In some embodiments, the compressible porous element can be substantially free of antimicrobial. In some embodiments, when inserted into the lumen, the elongate member can displace liquid in a lumen of the transfer set such that air transfers through the porous element and liquid is retained in the compressible porous element.

Disclosed herein are embodiments of a capping system for a medical connector that can include a base element containing a finger retainer on a distal end of the base element, a cap having a partially enclosed interior space, a proximal end and distal end, and a heat shrink band at a distal end of the cap and the proximal end of the base element, and providing a barrier to the interior of the cap. Disclosed herein are embodiments of a cap system for a medical connector that can include a base element containing a finger retainer on the distal end of the cap system, and a cap having a partially enclosed interior space, the cap having a proximal end and distal end. Also disclosed herein are embodiments of a cap system for a medical connector that can include a base element containing a finger retainer on a distal end of the cap system, a cap, and a heat shrink band at the distal end of the cap providing a barrier to a partially enclosed interior space of the cap.

Disclosed herein are embodiments of a method of retaining a cap on a base such that the cap cannot be reinstalled on the base. The method can include providing a cap system including a cap and removing the cap from the base such that the heat shrink band is retained on the base but the heat shrink band contracts to prevent reinstallation onto the base. The cap can include a partially enclosed interior space, a proximal end, and a distal end. The cap system can further include a base element containing a finger retainer on the proximal end of the cap and a heat shrink band at a distal end of the cap providing a barrier to the partially enclosed interior space of the cap. The cap can be secured to the base element by the heat shrink band, for example at or adjacent to a distal end of the cap.

Disclosed herein are embodiments of a method of delivering an antimicrobial to a medical connector that can include providing a medical connector having a lumen, an inner wall and a proximal end face, providing a cap having a proximal end and a distal end, with an opening on the distal end, an elongate member at least partially within an interior of the cap, and a dry antimicrobial on the elongate member, a dry compressible porous element substantially free of antimicrobial, and inserting the elongate member into a liquid contained within the lumen such that the dry antimicrobial dissolves into the liquid to create an antimicrobial liquid within the lumen and the porous element. In some embodiments, the antimicrobial liquid within the lumen can contact the inner wall, and the antimicrobial within the porous element can contact the proximal end face.

Disclosed herein are embodiments of a cap for a medical connector substantially as described herein or shown in the accompanying drawings. Also disclosed herein are embodiments of a method of using a cap for a medical connector substantially as described herein or shown in the accompanying drawings.

Any embodiments of the caps, methods, and systems disclosed herein can include, in additional embodiments, one or more of the following steps, features, components, and/or details, in any combination with any of the other steps, features, components, and/or details of any other embodiments disclosed herein: wherein medical connector is part of a peritoneal dialysis transfer set; wherein the sealing surface is located in an exterior direction from the threads; wherein the cap further includes a proximal cavity in the partially enclosed interior space; wherein a proximal cavity includes a portion of interior proximal to proximal end of transfer set when the cap is installed on a transfer set; wherein a porous element is included within the proximal cavity; wherein the porous element is dry prior to installation on a transfer set; wherein the porous element is free of any antiseptic or antimicrobial substance or other substance, prior to installation; wherein the porous element is configured to retain a fluid exiting the medical connector upon installation of the cap on the medical connector; wherein the proximal cavity encloses a volume greater than the volume of the elongate member displacing volume; wherein the porous element in the proximal cavity encloses a volume from 75 to 125 percent of the elongate member displacing volume; wherein the porous element in the proximal cavity encloses a volume from 50 to 150 percent of the volume of the elongate member displacing volume; wherein the proximal cavity includes one or more dividers to form sub-cavities; wherein the proximal cavity provides a fluid flow path for fluid to exit a lumen of the medical connector during installation of the cap; wherein the elongate member is contained entirely within the partially enclosed interior space of the cap; wherein the elongate member extends out a distal end of the partially enclosed interior space; wherein the sealing surface faces radially inward and is located in an exterior direction from the threads; wherein the cap further includes a distal planar sealing surface which faces distally and is located in an exterior direction from the threads; wherein the cap further includes a distal planar sealing surface and a distal radial sealing surface, the sealing surfaces located in an exterior direction from the threads; wherein the cap further includes a distal oblique sealing surface in an exterior direction from the threads; wherein the medical connector has a proximal end and the elongate member has a displacing volume defined as a volume of the elongate member that is distal to the proximal end of the medical connector when the cap is fully installed on the medical connector; wherein the medical connector has a proximal end and the proximal cavity can include a volume of the partially enclosed interior space of the cap proximal to the proximal end of the medical connector when the cap is installed on a medical connector; and/or wherein the medical connector has a proximal end, and the partially enclosed interior space has a distal cavity that can include volume of the partially enclosed interior space distal to the proximal end of the medical connector and proximal to a seal between the cap and medical connector and radially outward from an outer wall of a transfer set when the cap is installed on the medical connector.

Any embodiments of the caps, methods, and systems disclosed herein can include, in additional embodiments, one or more of the following steps, features, components, and/or details, in any combination with any of the other steps, features, components, and/or details of any other embodiments disclosed herein: wherein the elongate member does not form a fluid seal within a lumen of the medical connector; wherein the cap is configured to not a seal within a lumen of the medical connector; wherein the cap further includes a cap retention flange for securing the cap to a base; wherein a cap for a medical connector has a partially enclosed interior space, an elongate member positioned at least partially within the partially enclosed interior space, an antimicrobial on or in the elongate member, threads on the cap for securing the cap to the medical connector, and a sealing surface on the cap, the sealing surface located distal to the threads and providing a primary seal between the cap and the medical connector when the cap is installed on the medical connector; wherein the sealing surface is located in an exterior direction from the threads; wherein the cap further includes a proximal cavity in the partially enclosed interior space; wherein the cap can include a porous element within the proximal cavity; wherein the elongate member is contained entirely within the partially enclosed interior space of the cap; wherein the first sealing capacity is more than 75 percent of a total sealing capacity between the cap and the medical connector when the cap is installed on the medical connector; wherein the first sealing capacity is more than 90 percent of a total sealing capacity between the cap and the medical connector when the cap is installed on the medical connector; wherein the first sealing capacity is more than 95 percent of a total sealing capacity between the cap and the medical connector when the cap is installed on the medical connector; and/or wherein the cap is configured to not a seal within a lumen of the medical connector Any embodiments of the caps, methods, and systems disclosed herein can include, in additional embodiments, one or more of the following steps, features, components, and/or details, in any combination with any of the other steps, features, components, and/or details of any other embodiments disclosed herein: wherein the sealing surface is a primary sealing surface; wherein the cap is configured to not a seal within a lumen of the medical connector; wherein the sealing surface is located distal to the threads and providing a first sealing capacity when installed on the medical connector, the first sealing capacity is more than 50 percent of a total sealing capacity between the cap and the medical connector when the cap is installed on the medical connector; wherein the sealing surface is located distal to the threads and providing a first sealing capacity when installed on the medical connector, the first sealing capacity is more than 75 percent of a total sealing capacity between the cap and the medical connector when the cap is installed on the medical connector; wherein the sealing surface is located in an exterior direction from the threads; wherein the cap further includes a proximal cavity; wherein further can include a porous element within the proximal cavity; wherein the elongate member is contained entirely within a partially enclosed interior space of the cap; wherein the cap further includes a proximal cavity in the partially enclosed interior space; wherein further can include a porous element within the proximal cavity; wherein the porous element encloses a volume from 75 to 125 percent of the elongate member displacing volume; wherein the porous element encloses a volume from 50 to 150 percent of the volume of the elongate member displacing volume; wherein further can include a silver-based antimicrobial; wherein the silver-based antimicrobial is coated onto portions of the cap; wherein the silver-based antimicrobial is integrally formed into at least a portion of the cap; wherein the silver-based antimicrobial includes a silver salt; wherein the silver-based antimicrobial includes a silver complex; wherein the silver-based antimicrobial includes silver ions; wherein the silver-based antimicrobial includes silver nano particles; wherein the silver-based antimicrobial includes a silver nano layer; wherein the silver-based antimicrobial includes pentasilver hexaoxoiodate, silver-sulfadiazine, silver trifluoroacetate, silver nitrate, silver stearate, and combinations thereof; wherein the antimicrobial includes chlorhexidine acetate; wherein the cap includes chlorhexidine acetate and a silver-based antimicrobial.

BRIEF DESCRIPTION OF THE FIGURES

FIG. 13 is a side view of an embodiment of a peritoneal dialysis cap being installed on a hub or end portion of a transfer set.

FIG. 14 is a cross-sectional view of the peritoneal dialysis cap being installed on a hub or end portion of a transfer set as shown in FIG. 13, taken along line H-H as shown in FIG. 13.

DETAILED DESCRIPTION

Figure 1:
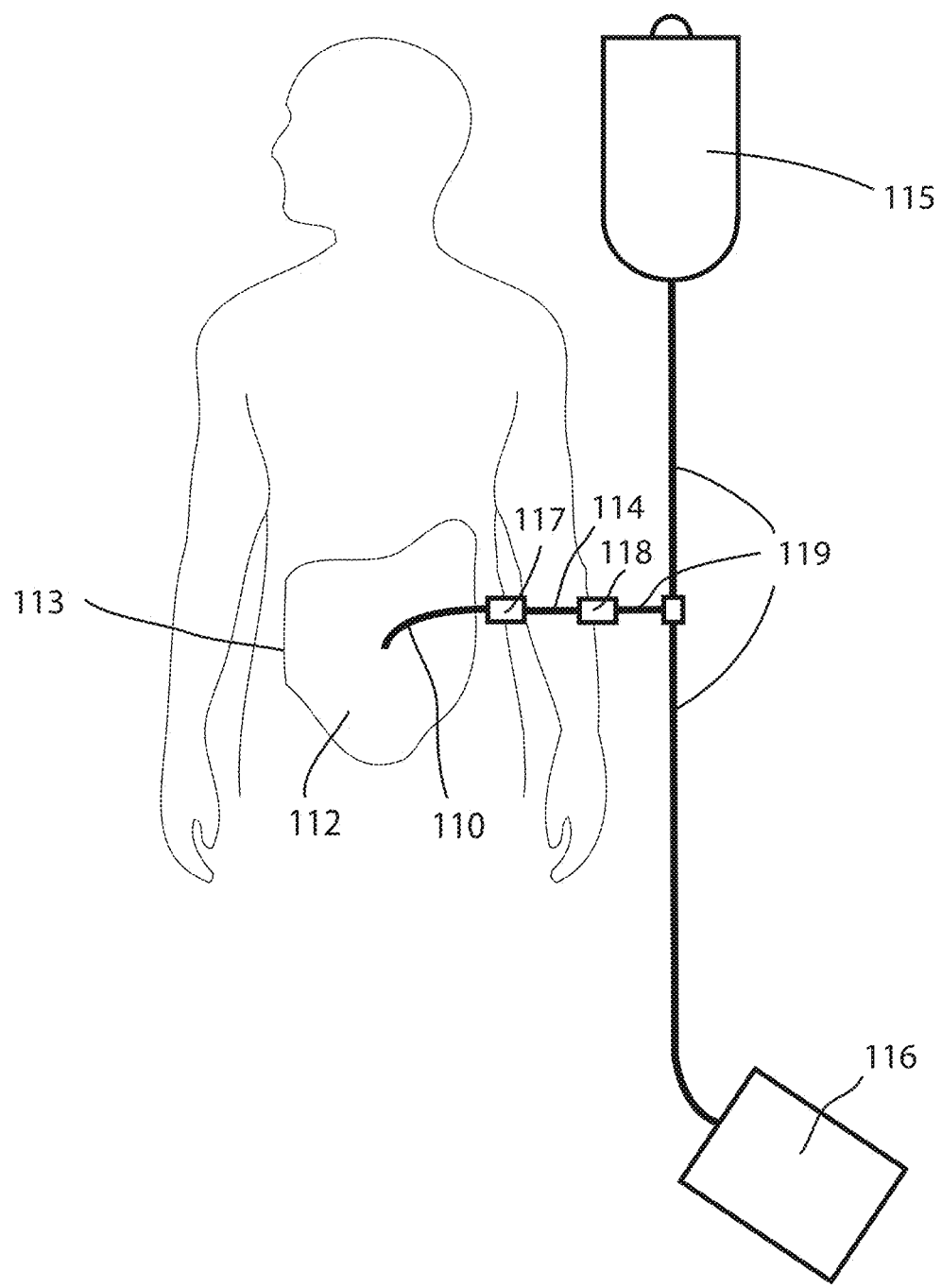
FIG. 1 is a schematic illustration of a patient undergoing peritoneal dialysis, showing a peritoneal catheter extending into a peritoneal cavity into which a dialysis solution is injected and then removed.

Referring now to the drawings, FIG. 1 is a schematic diagram of a patient undergoing peritoneal dialysis, showing a peritoneal catheter 110 extending into a peritoneal cavity 112 (surrounded by peritoneum 113) of a patient, into which a dialysis solution from source bag 115 flows into the patient. The dialysis solution can later then be drained into drain bag 116. The peritoneal catheter 110 can be in fluid communication with the bags 116 and 115 by means of a transfer set 114 and an infusion set 119. Couplings 117 and 118 can be positioned on either end of the transfer set 114. In some examples, the transfer set 114 can be the peritoneal dialysis transfer set 119 as described.

Figure 2:
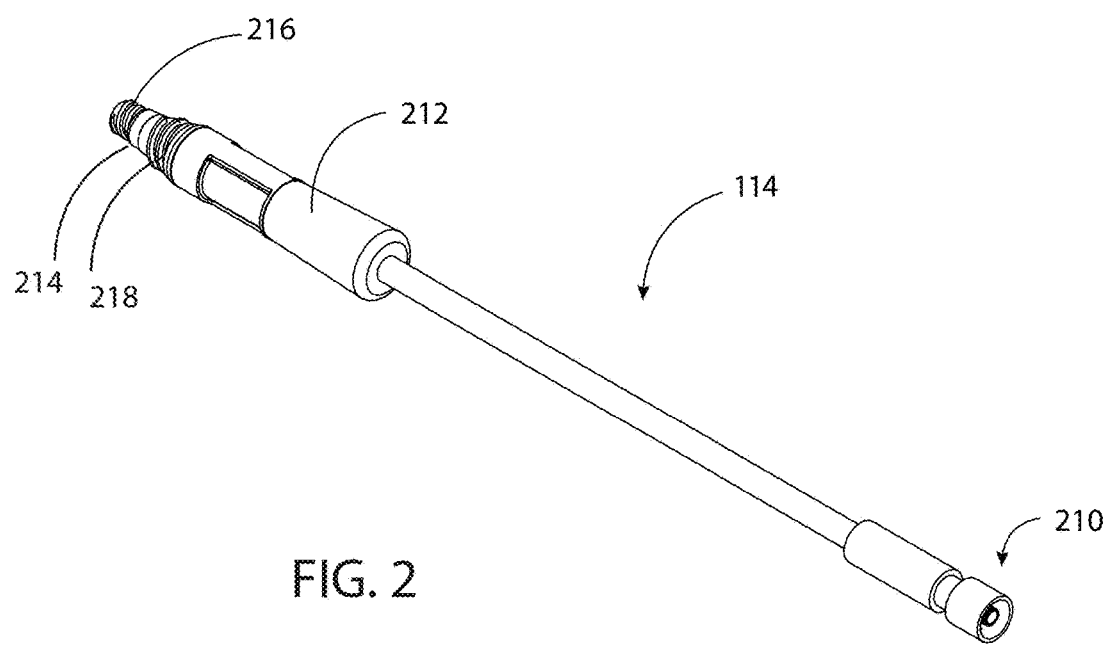
FIG. 2 is a perspective view of a peritoneal dialysis transfer set.
Figure 3:
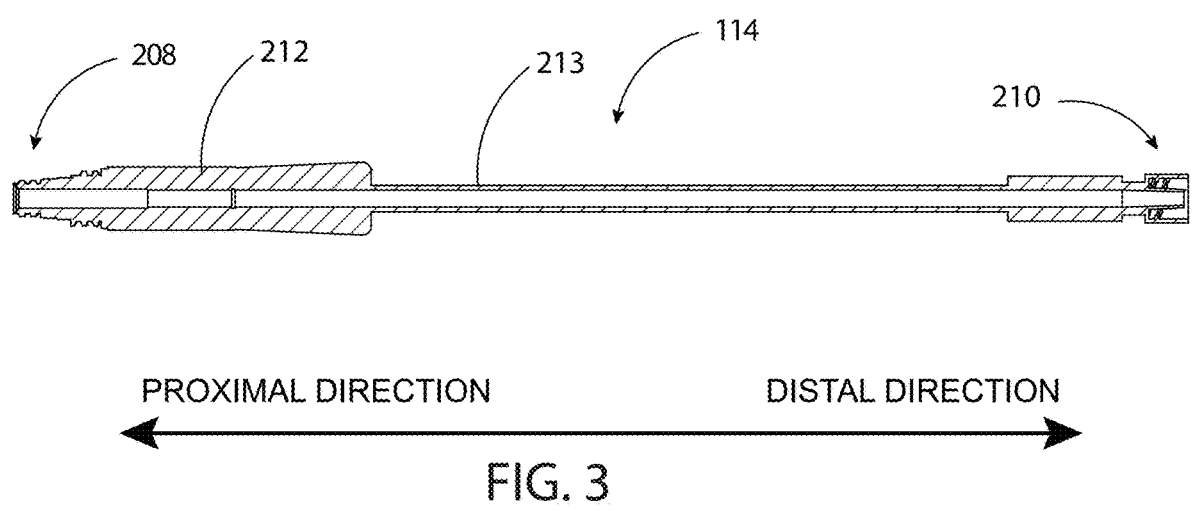
FIG. 3 is a cross-sectional view along a longitudinal centerline of the peritoneal dialysis transfer set of FIG. 2.

FIG. 2 is a perspective view of a peritoneal dialysis transfer set 114, and FIG. 3 is a section-view of the peritoneal dialysis transfer set 114. The peritoneal dialysis transfer set 114 can include tubing 213 extending from a proximal end 208 of the transfer set 114 to the distal end 210. At the proximal end 208 of the transfer set 114 can be a threaded male connector 214 with first male threads 216 and second male threads 218. The threaded male connector 214 is a proximal end portion of the peritoneal dialysis transfer set 110.

During the exchange process, the waste dialysis solution can flow from the peritoneal cavity 112 to the coupling 117 and transfer set 114, then through the coupling 118 and finally through the lower portion of the infusion set 119 into the drain bag 116. After the exchange process is complete, the infusion set 119 can be separated at coupling 118 from transfer set 114 and the female connector of the transfer set 114 can be capped until the next dialysis solution exchange is initiated (not shown). Thus, in a typical peritoneal dialysis, the exchange process can be initiated by removing a cap from the distal end 210 of the transfer set 114 and then by joining to the infusion set 119 to form the coupling 118. This process can be reversed at the end of the exchange process by removing the infusion set 116 at coupling 118 and installing a new cap.

Figure 4:
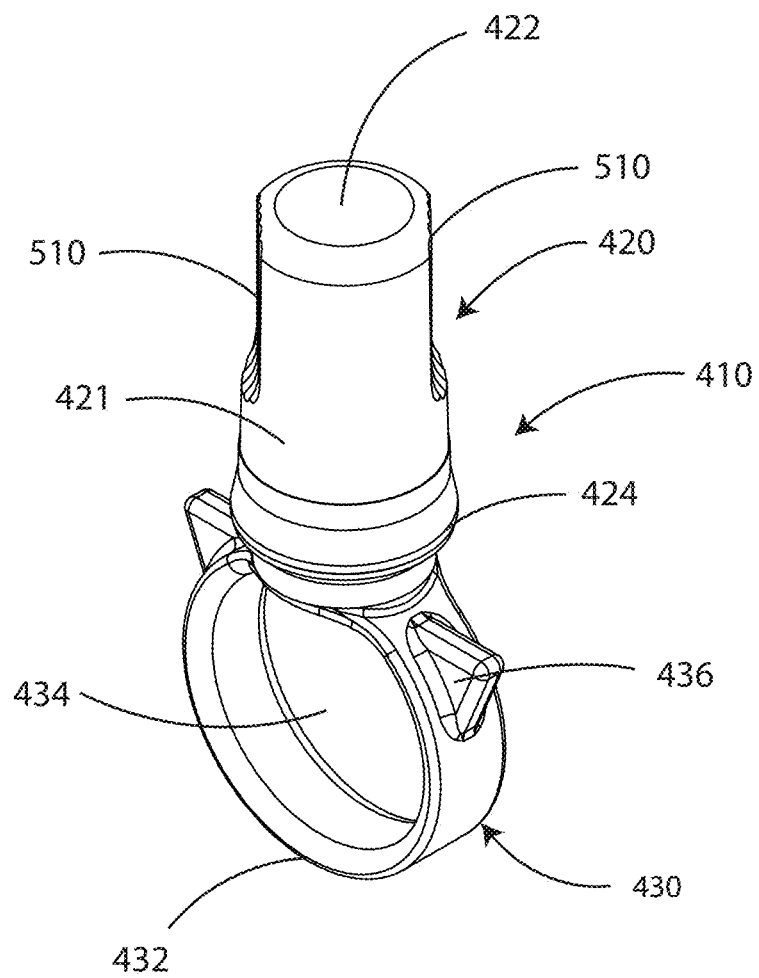
FIG. 4 is a perspective view of an embodiment of a cap combination set including a peritoneal dialysis cap and a base element.

FIG. 4 is a perspective view of an embodiment of a cap combination set 410 comprising a peritoneal dialysis cap 420 and a base element 430. Some embodiments of the peritoneal dialysis cap 420 can have a proximal end 422 and a distal end 424. The base element 430 can include a ring 432 sized to receive a finger of a user, with a hole 434 through the ring 432. In addition, in the embodiment depicted, the base element 430 can include a pair of side extensions 436 that can restrict rotation of the base element 430 when the base element 430 is positioned on a user's hand. For example and without limitation, in some embodiments, a user can press against one or both of the side extensions 436 to increase a torque force applied to the base element 430. In some embodiments, the side extensions 436 can have a pointed or triangular shape, as shown, a rounded shape, or any other desired shape.

Figure 5:
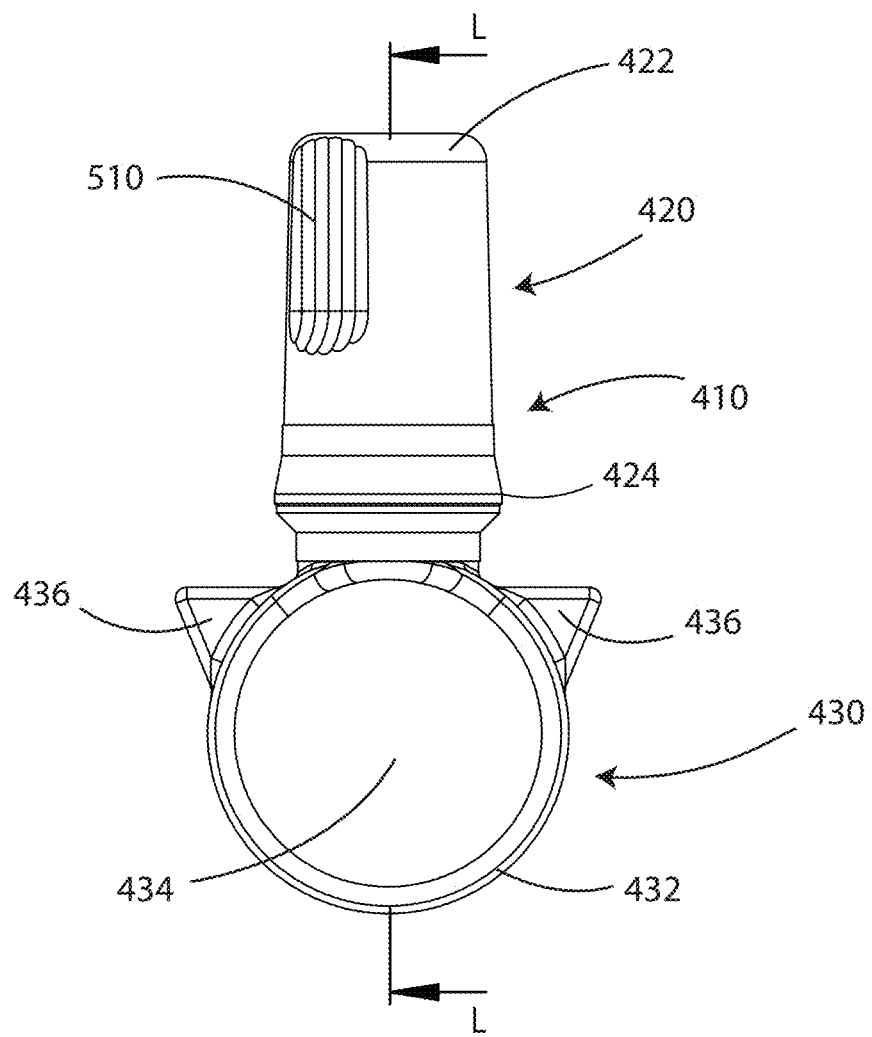
FIG. 5 is a front view of the embodiment of the cap combination set shown in FIG. 4.

In any embodiments disclosed herein, the cap 420 can have one or more gripping portions 510 on an outside surface of the body 421 of the cap 420. In some embodiments, the gripping portion(s) 510 can be positioned at or adjacent to the proximal end 422 of the cap 420 and can extend along a length of an outside surface of the cap in an axial direction. As shown, some embodiments of the cap 420 can have two gripping portions 510 formed in the body 421 of the cap 420 that are mutually opposed. With reference to FIG. 5, in some embodiments, the gripping portion 510 can have channels, ridges, roughened texture, or other features configured to improve the grip of a user's fingers on the cap 420 during use of the cap 420.

FIG. 5 is a side view of the embodiment of the cap combination set 410 shown in FIG. 4, and can include the peritoneal dialysis cap 420 and the base element 430. The peritoneal dialysis cap 420 can have a proximal end 422 and a distal end 424. The base element 430 can include a ring 432 sized to receive the finger of a user, with a hole 434 through the ring 432. In addition, in the embodiment depicted, the base element 430 can include a pair of side extensions 436, as described above.

Figure 6:
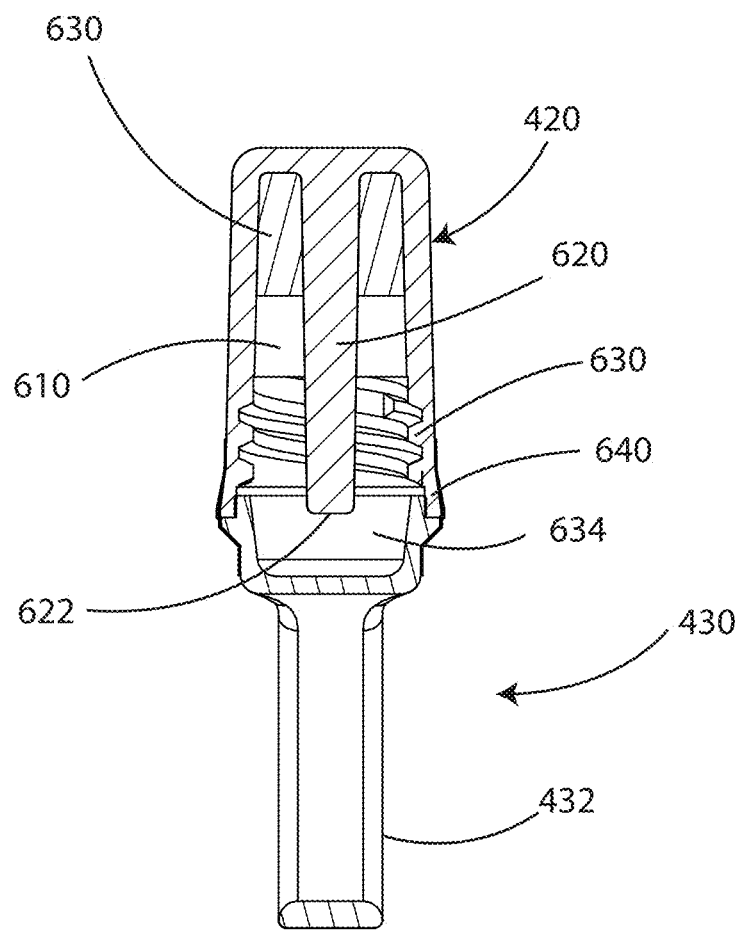
FIG. 6 is a cross-sectional view of the embodiment of the cap combination set shown in FIG. 4, taken along line L-L as shown in FIG. 5.

FIG. 6 is a cross-sectional view of the embodiment of the cap combination set 410 containing a peritoneal dialysis cap 420 and base element 430. The base element 430 can include a ring 432 sized to receive the finger of a user, with a hole 434 through the ring 432. Some embodiments of the peritoneal dialysis cap 420 can include an internal volume 610 from which an elongate member 620 can extend, the elongate member having a distal end 622. Some embodiments of the cap 420 can have a porous element 630 which can include a sponge material, an open cell foam material, or other suitable dry foam or dry porous material. In some embodiments, the porous element 630 can have an opening therein configured to receive the elongate member 622 therein. The porous element 630 can be positioned so as to abut against a proximal wall of the cap and the inside side walls of the cap. The porous element 630 can be expandable and compressible and can, in some embodiments, have an outer diameter that is larger than an inner diameter of the cap so that the porous element expands against the inside wall of the cap when coupled with or otherwise assembled with the cap. The porous element 630 can be coupled the cap so as to be positioned in contact with an inside surface of the proximal end of the cap.

In some embodiments, the porous element 630 can be positioned at a base of the elongate member 620, at a proximal end portion of the internal volume 610, and/or anywhere within the internal volume 610. For example and without limitation, in some embodiments, the porous element 630 can be positioned at a base of the elongate member 620 and can have an opening therein that can be sized and configured to pass over the elongate member 620 such that, when the porous element 630 is positioned in an operable position (e.g., at a proximal end of the internal volume 610), the elongate member 622 can extend through the opening in the porous element 630.

In some embodiments, the space occupied by or the volume of the porous element 630 can be a sub-portion of the internal volume 610. In other words, the porous element 630 can, in some embodiments, occupy less than the entire volume of the internal volume 610. In some embodiments, the porous element 630 can, in some embodiments, occupy 25% or approximately 25% of the volume of the internal volume 610 of the cap, or can, in some embodiments, occupy from 20% or approximately 20% or less than 20% to 50% or approximately 50% or more than 50% of the internal volume 610 of the internal volume 610 of the cap, or can, in some embodiments, occupy from 30% or approximately 30% to 40% or approximately 40% of the internal volume 610 of the internal volume 610 of the cap, or of any value within any of the foregoing ranges or from and to any values within any of the foregoing ranges, with the volume of the internal volume 610 of the cap being determined before a separate connector is advanced into the internal volume 610 (i.e., of the cap before it has been connected to a catheter). In some embodiments, the volume within the internal volume 610 is greater than a volume of liquid within the hub or connector that the elongate member 620 is configured to displace when the elongate member 620 is advanced into the hub or connector.

In any embodiments disclosed herein, the porous element 630 can be configured to absorb and retain liquid that that comes into contact with the porous element 630, at least until the porous element 630 becomes saturated with liquid. In some embodiments, the porous element 630 can have sponge-like characteristics. In this arrangement, the porous element 630 can absorb and retain liquid that is expelled from the hub of the catheter or transfer set as the cap is engaged with the hub to reduce the likelihood that liquid will be leaked from the cap as the cap is engaged with the hub of the catheter. Additionally, because the antimicrobial can be dissolved into the liquid as the cap is engaged with the hub, the liquid that can be absorbed by the porous element 630 can contain antimicrobial, so as to provide further disinfection capabilities to the porous element 630 and to other surfaces as any liquid, if any, is expelled from the porous element.

Figure 7:
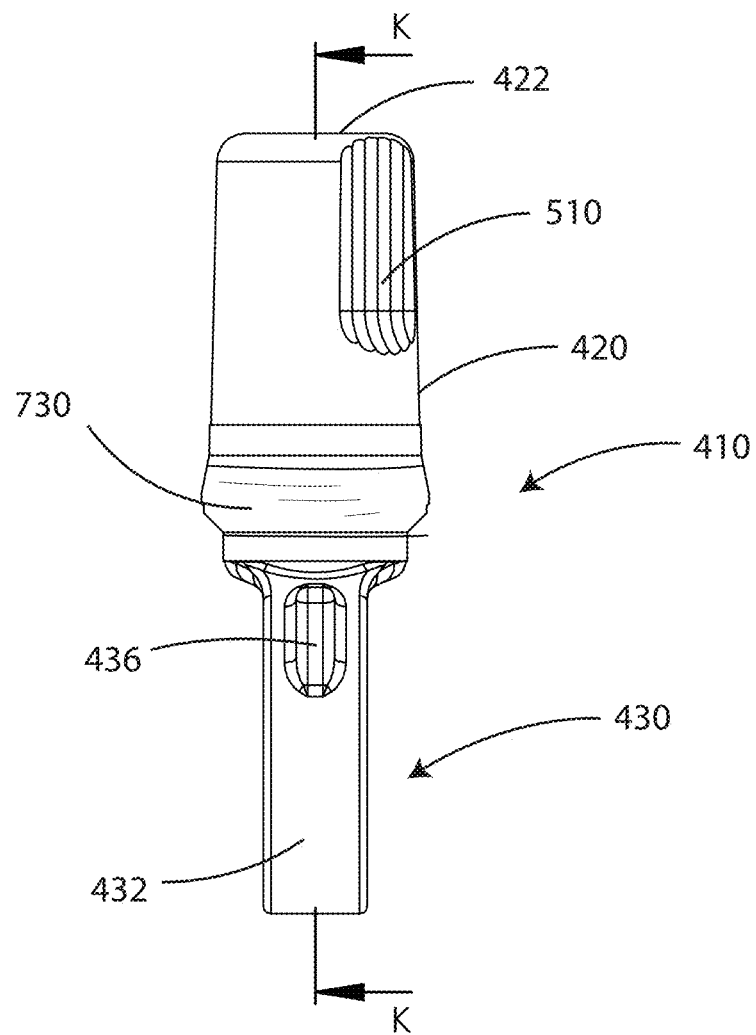
FIG. 7 is a side view of the embodiment of the cap combination set shown in FIG. 4.

FIG. 7 is a side view of the embodiment of the cap combination set 410 containing a peritoneal dialysis cap 420 and base element 430, including one or more gripping portions 510 and a sealing band 730. As shown, any embodiments disclosed herein can include a sealing band 730 to secure the peritoneal dialysis cap 420 to the cap base element 430. The sealing band can retain the peritoneal dialysis cap 420 to the base element 430 prior to use or inhibit the detachment of the cap 420 from the base element 430 prior to use, and/or can prevent re-installation of the peritoneal dialysis cap 420 onto the base element 430 after the cap 420 has been detached from the base element 430 to prevent or inhibit the reuse of the cap 420 (which may not be sanitary). The peritoneal dialysis cap 420 can include a proximal end 422 and a distal end 424. The base element 430 can include a ring 432 sized to receive the finger of a user, the ring 432 having an opening 434 sized and configured to receive the finger of a user through the ring 432. In addition, in the embodiment depicted, the base element 430 can include a pair of side extensions 436, as described above. In some embodiments, the side extensions 436 can allow a user to exert a greater level of torque on the base element 430 when the base element 430 is positioned on a user's hand.

Figure 8:
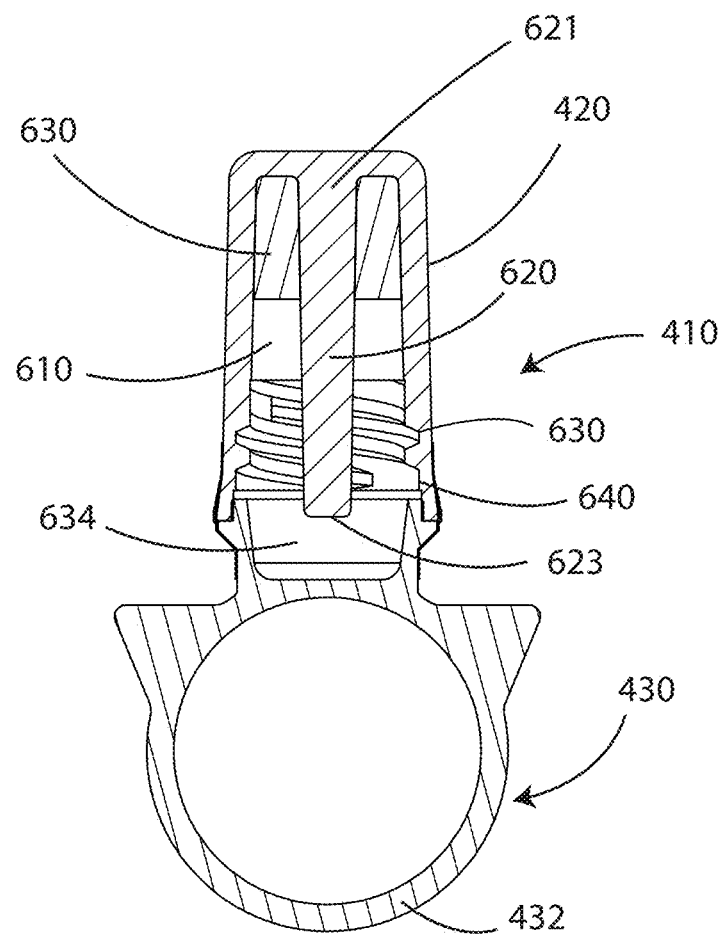
FIG. 8 is a cross-sectional view of the embodiment of the cap combination set shown in FIG. 4, taken along line K-K as shown in FIG. 7.
Figure 9:
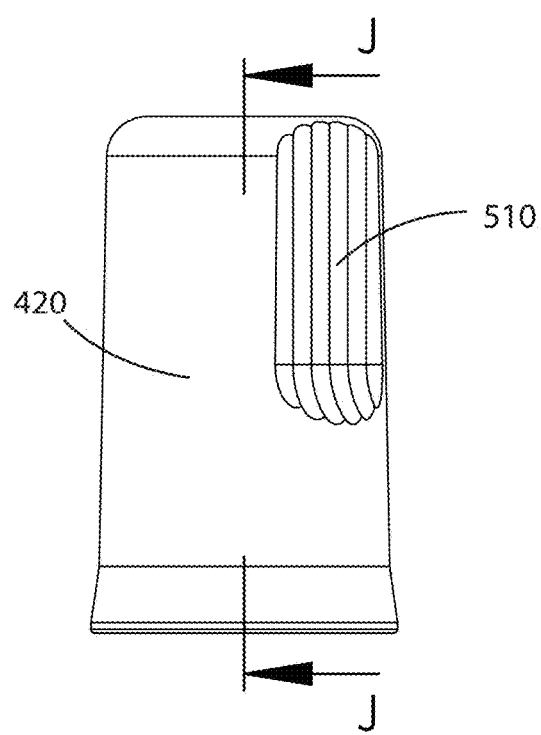
FIG. 9 is a side view of an embodiment a peritoneal dialysis cap.
Figure 10:
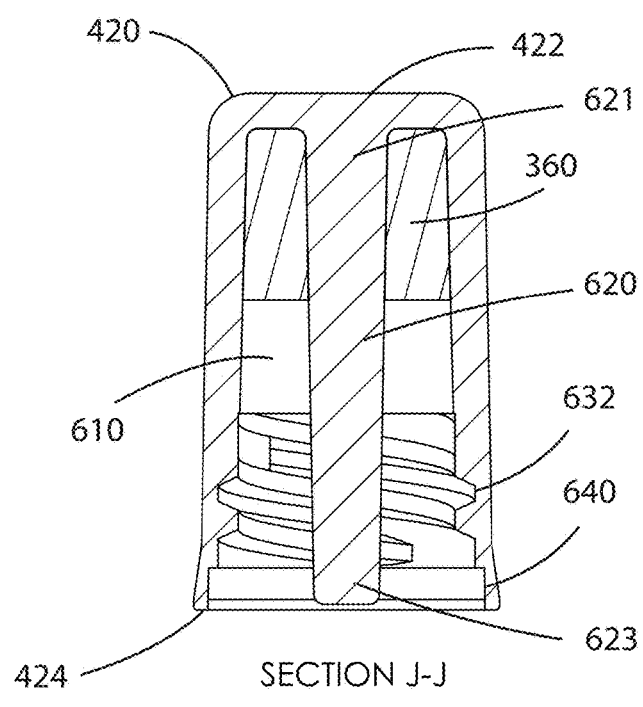
FIG. 10 is a cross-sectional view of the embodiment of the peritoneal dialysis cap set shown in FIG. 9, taken along line J-J as shown in FIG. 9.

FIG. 8 is a cross-sectional view of the embodiment of the cap combination set 410 including the peritoneal dialysis cap 420 and base element 430 as shown in FIG. 5, taken along line K-K of FIG. 7. FIG. 9 is a side view of a peritoneal dialysis cap 420 in accordance with various embodiments herein, including showing a gripping portion 510. FIG. 10 is a side cross-sectional view of a peritoneal dialysis cap of FIG. 9, taken along line J-J as shown in FIG. 9. As illustrated in FIG. 10, in some embodiments, the diameter or horizontal cross-sectional width of the elongate member 620 can be larger than the horizontal cross-sectional width of the side wall(s) of the cap 420 and/or the vertical width of the proximal end 422 of the cap 420. For example, as shown, on at least one point along the elongate member, or along at least a majority of the vertical length of the elongate member 620, and/or along the entire vertical length of the elongate member 620, the diameter or horizontal cross-sectional width of the elongate member 620 can be larger than the horizontal cross-sectional width of some point and/or of every point along the vertical length of the side wall(s) of the cap 420, and/or of some point and/or of every point on the vertical width along the horizontal length of the proximal end 422 of the cap 420. As illustrated, the outer surface of the cap 420 can be tapered outwardly at the distalmost end of the cap 420.

As shown in many figures, in some embodiments, the elongate member 620 can be solid (not hollow) and/or can be formed unitarily with the side wall(s) of the cap 420 and/or the proximal end 422 of the cap 420, without providing separately formed components that are brought together. As shown, the elongate member 620 can be sufficiently long that it extends to about the distal end of the cap 420 and/or the elongate member 620 can be slightly shorter than the full vertical length of the side wall of the cap 420. By making the elongate member 620 shorter than the side wall of the cap 420, the elongate member 620 is less likely to be contaminated if a user (improperly) rests the cap 420 on a surface before use. Also, in some embodiments, when the elongate member 620 is shorter than the side wall of the cap 420, the cap 420 can be provided with a removable adhesively attached lid or seal (not shown) that extends across the distal opening of the side wall of the cap 420 to resist contamination of the interior of the cap 420 before use. As shown, the distalmost end of the threaded interior portion of the cap 420 can be proximal from the distalmost end of the side wall of the cap 420, and the portion of the side wall that is distal of the distalmost end of the threaded interior portion of the cap 420 can be thinner in horizontal cross-sectional width than horizontal cross-section of the portion of the side wall that is proximal from the threaded interior portion of the cap 420. This thinner portion can provide some degree of flexibility to enable slight movement or temporary radial expansion of the distal end of the cap 420 when attached to the hub 212 to assist in forming a seal between the cap 420 and the hub 212.

In some embodiments, as illustrated, the porous element 630 can surround the base of the elongate member 620 along at least a majority of the interior region between the base of the elongate member 620 and the proximal end of the threaded region on the interior of the cap 420. As shown, the vertical height or thickness of the porous element 630 can be at least as large as the distance between the proximal and distal ends of the threaded region of the cap 420. In some embodiments, as shown, the fluid absorption volume of the porous element 630 can be at least as great as the volume of the elongate member 420 to enable the porous element 630 to absorb any fluid that is displaced by insertion of the elongate member 420 into a hub 212 that is already filled with fluid.

Some embodiments of the peritoneal dialysis cap 420 can include an internal volume 610 through which an elongate member 620 can extend. The internal volume 610 can extend from a proximal end 422 of the body 421 of the cap 420 to a distal end 424 of the body 421 of the cap 420. As mentioned, the elongate member 620 can extend through a longitudinally axial centerline of the body 421 of the cap 420 and the internal volume 610 of the cap 420.

The elongate member 620 can have a proximal end 621 adjacent to the proximal end 422 of the cap 420 and can extend to a distal end 623 along a longitudinally axial centerline of the internal volume 610. In some embodiments, the elongate member 620 can have a round cross-sectional shape, as shown, or any other desired cross-sectional shape, such as a star shape, hexagonal shape, octagonal, or other polygonal shape. The elongate member 620 can be uniform along a length thereof, or can taper along all or a portion of a length thereof such that a diameter or cross-sectional size of the elongate member 620 at the distal end 623 thereof is less than a diameter or cross-sectional size of the elongate member 620 at the proximal end 621 thereof. In some embodiments, the elongate member 620 can extend to a length or to a point or plane that is less than a length of the cap 420 at a distal end 424 thereof so that the distal end 623 of the elongate member 620 does not extend past the distal end 424 of the cap 420.

In some embodiments, the elongate member 620 can be integrally (i.e., monolithically) formed with the body 421 of the cap 420. In some embodiments, the elongate member 620 can be separately formed and coupled with the body 421 of the cap 420.

In some embodiments, a porous element 630 can be positioned at the proximal end of the internal volume 610 of the peritoneal dialysis cap 420. In addition, at the distal end of the peritoneal dialysis cap 420 is a is an overlapping region 640 that has a flange that engages the base element 430. The base element 430 in the depicted configuration can include a recess 634 into which the proximal end 622 of the elongate member can extend.

Figure 11:
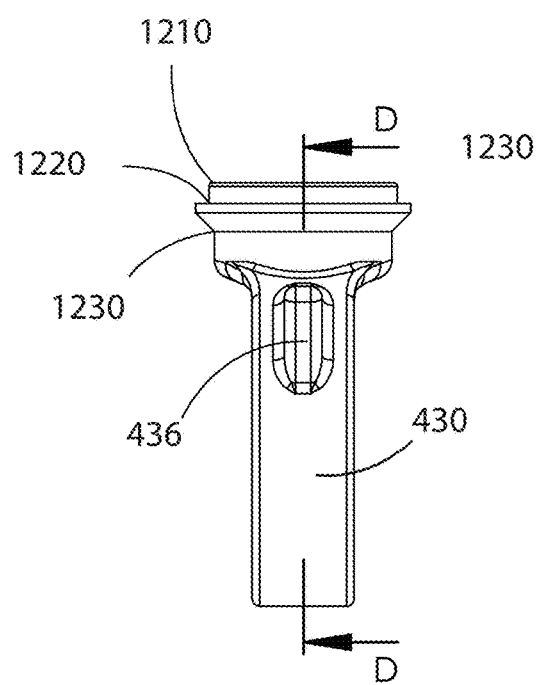
FIG. 11 is a side view of an embodiment of a peritoneal dialysis cap base.
Figure 12:
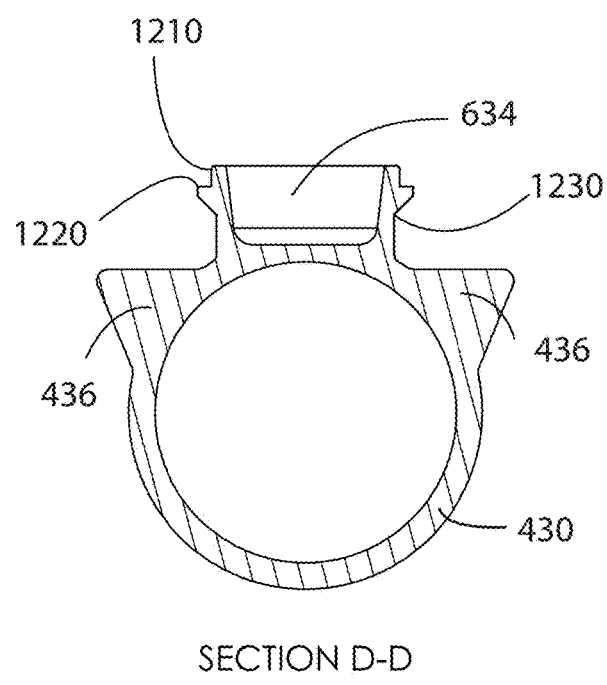
FIG. 12 is a cross-sectional view of the embodiment of the peritoneal dialysis cap base element shown in FIG. 11, taken along line D-D as shown in FIG. 11.

FIG. 11 is a side view of an embodiment of a peritoneal dialysis base element 430. FIG. 12 is a side cross-sectional view of the peritoneal dialysis base element 430 of FIG. 11, taken along line D-D shown in FIG. 11. The base element 430 can include a ring 432 sized to receive the finger of a user, with a hole 434 through the ring 432. The base element 430 further can include a recess 634 into which the distal end 623 of the elongate member 620 (not shown) can extend into when the cap 420 is coupled with the base element 430. In some embodiments, the base element 430 can include an upper flange surface 1210 and a lower flange surface 1220, along with an outer flange surface 1230.

FIG. 13 is a side view of an embodiment of a peritoneal dialysis cap 420 being installed on a proximal hub 212 of a transfer set. FIG. 14 is a cross-sectional view of the embodiment of the peritoneal dialysis cap 420 shown in FIG. 13 being installed on the proximal hub 212 of the transfer set, taken along line H-H shown in FIG. 13. As the cap 420 is being advanced into engagement with the hub 212, the cap 420 can be rotated so that the threads 632 of the cap 420 rotate to engage the threads 216 of the proximal hub 212 of a transfer set. As the cap 420 is being advanced into engagement with the hub 212, the elongate member 620 can extend into a passageway 217 of the proximal hub 212 of the transfer set. The elongate member can project into the interior or passageway 217 of the proximal hub 212 of the transfer set as the body 421 of the cap 420 moves into position over threads 216 on the proximal hub 212 of the transfer set.

Figure 15:
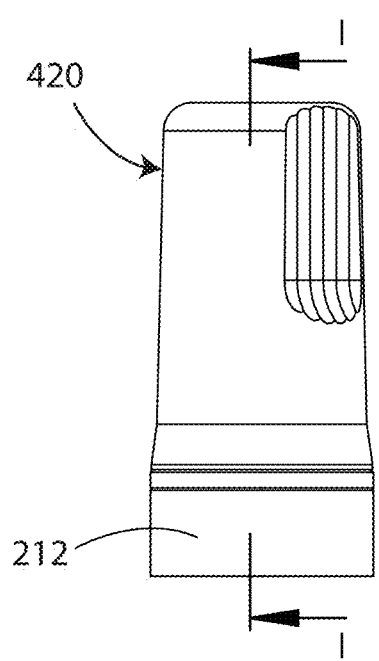
FIG. 15 is a side view of an embodiment of a peritoneal dialysis cap installed on a hub or end portion of a transfer set.
Figure 16:
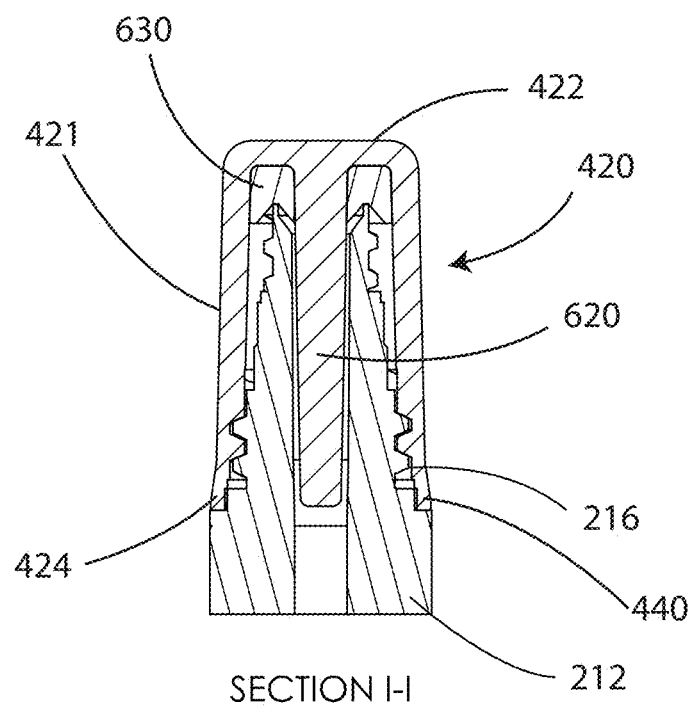
FIG. 16 is a cross-sectional view of the embodiment of the peritoneal dialysis cap installed on a hub or end portion of a transfer set as shown in FIG. 15, taken along line I-I as shown in FIG. 15.
Figure 17:
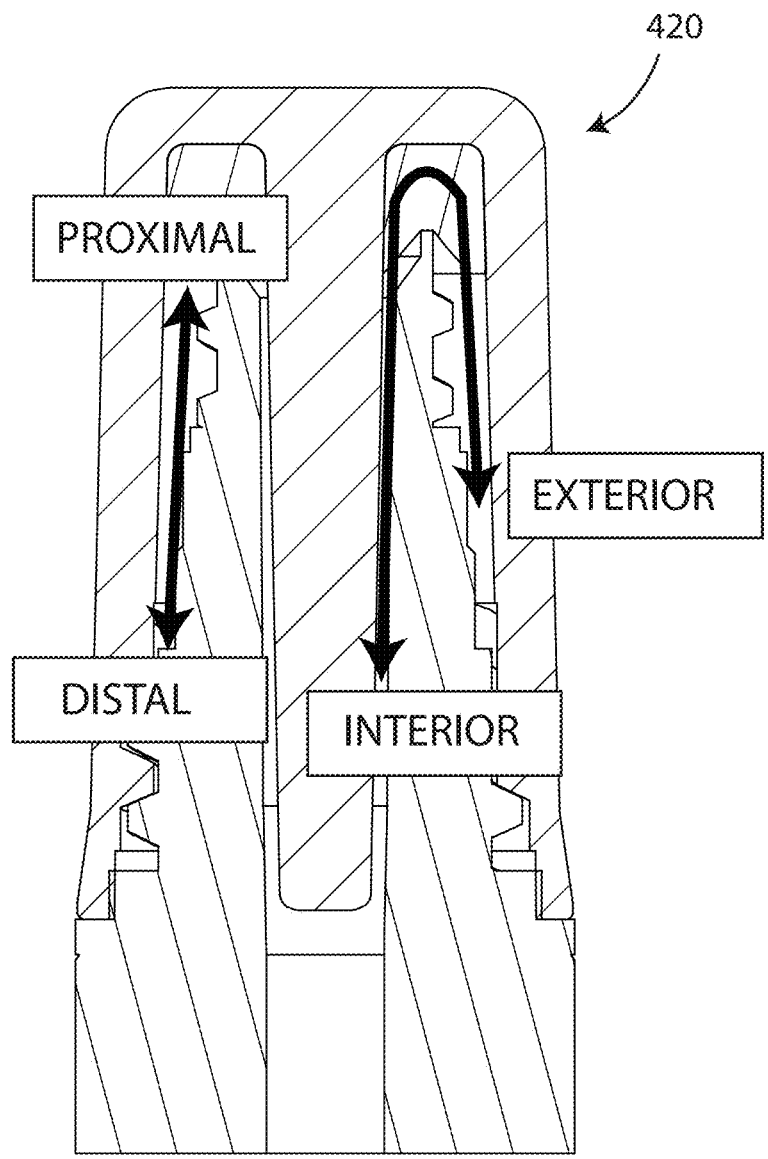
FIG. 17 is a cross-sectional view of an embodiment of a peritoneal dialysis cap installed on a hub or end portion of a transfer set in accordance with various embodiments herein, showing proximal/distal orientations and interior/exterior orientations.

FIG. 15 is a side view of an embodiment of a peritoneal dialysis cap 420 installed on an exemplifying proximal hub 212 of a transfer set. FIG. 16 is a cross-sectional view of the embodiment of the peritoneal dialysis cap 420 installed on the proximal hub 212 of the transfer set, taken along line I-I as shown in FIG. 15. FIG. 17 cross-sectional view of an embodiment of the peritoneal dialysis cap 420 installed on a transfer set in accordance with various embodiments herein, showing proximal/distal orientations and interior/exterior orientations. The elongate member 620 on the peritoneal dialysis cap 420 can extend into the lumen of the transfer set, and the threads 632 of peritoneal dialysis cap 420 can engage the corresponding threads 216 of the transfer set.

In any embodiments disclosed herein, the cap can have one or more sealing surfaces, or two or two or more sealing surfaces configured to provide a liquid-tight seal between the cap and the medical connector that the cap is engaged with when the cap is engaged with the medical connector. In some embodiments, the one or more sealing surfaces can be configured to seal against an outer surface (such as an outer diameter) of the hub of the catheter or transfer set. In some embodiments, the one, two, or more sealing surfaces can be located distal to the threads and can provide a liquid-tight seal between the cap and the medical connector when the cap is installed on the medical connector.

In some embodiments, the cap 420 can have an overlapping region 640 at a distal end of the cap 420 that can overlap one or more portions or surfaces of the hub of the catheter or transfer set. In some embodiments, the overlapping region 640 can have a sealing flange 440 that engages the base element 430 and/or one or more surfaces of the hub of a catheter or the transfer set. Some embodiments of the cap 420 can have one or more sealing surfaces at a distal end 424 of the body 421 of the cap 420.

For example and without limitation, with reference to FIGS. 13-16, some embodiments of the cap 420 can have a sealing flange 440 at a distal end 424 of the body 421 of the cap 420. In some embodiments, the sealing flange 440 can have a first or distal sealing surface 442 that can be configured to engage with and seal against a first surface 219 of the proximal hub 212 of a transfer set. In some embodiments, the first or distal sealing surface 442 can be configured to abut against the first surface 219 in an axial direction as the cap 420 is threadedly engaged with the proximal hub 212 to create a seal against the first surface 219 of the proximal hub 212 of the transfer set. In some embodiments, the first sealing surface 442 can have a planar end surface that is approximately perpendicular to a longitudinally axial centerline of the cap 420 and that is configured to abut against the first surface 219 of the proximal hub 212 of the transfer set.

In some embodiments, the sealing flange 440 can have a second or radial sealing surface 444 that can be configured to engage with and seal against a second surface 221 of the proximal hub 212 of a transfer set. In some embodiments, the second or radial sealing surface 444 can be configured to constrict or squeeze in a radially inward direction against the second surface 221 to create a seal against the second surface 221 of the proximal hub 212 of the transfer set. For example and without limitation, in some embodiments, the sealing flange 440 can be configured to create an interference fit relative to the second surface 221 of the proximal hub 212 by have an inner diameter that is less than an outer diameter of the second surface 221 of the proximal hub 212. In some embodiments, without limitation, the sealing flange 440 can be configured to create an interference fit relative to the second surface 221 of the proximal hub 212 by have an inner diameter that is 5% or approximately 5% less than, or 10%, approximately 10%, or more than 10% less than, or from 2% or approximately 2% to 15% or approximately 15% less than an outer diameter of the second surface 221 of the proximal hub 212.

As illustrated in FIG. 16, in some embodiments the cap 420 and/or at least the threaded region of the interior of the cap 420 can be substantially rigid, and not generally elastomeric, resilient, and/or flexible, such that the threaded region does not change shape and/or expand during or after attachment to the hub 212. When the cap 420 is attached to the hub 212, the cap 420 can form a seal against the hub 212 by tightly, snuggly, forcible, securely, and/or frictionally contacting the hub 212 in a radial direction and/or in a longitudinal direction as shown. For example, in some embodiments, the cap 420 can be configured to resist venting at a normal fluid or air pressure within the hub 212 that is within the range of expected pressure of a peritoneal dialysis or hemodialysis catheter in normal use, such as an average blood pressure of a patient. In some embodiments, the pressure-resistance of the cap 420 when attached to the hub 212 can be substantially higher, such as at least about 10 psi, or at least about 20 psi, to provide increased protection against leaking when attached.

Any embodiments of the cap disclosed herein can be configured such that no seal or obstruction is created against an inside surface of the hub or connector (such as an inner passageway) that the cap is engaged with, even when the cap is fully engaged with the hub or connector. Any embodiments of the cap can be configured such that the cap only seals against an outside or outwardly facing surface of the hub or connector that the cap engages with, even when the cap is fully engaged with the hub or connector. In some embodiments, the cap can be configured such that there are no sealing surfaces at or adjacent to a proximal end portion of the elongate member. In some embodiments, the cap can be configured such that all sealing surfaces or seals are positioned at or adjacent to a distal portion of the cap, adjacent to an opening in the distal end of the cap.

Figure 18:
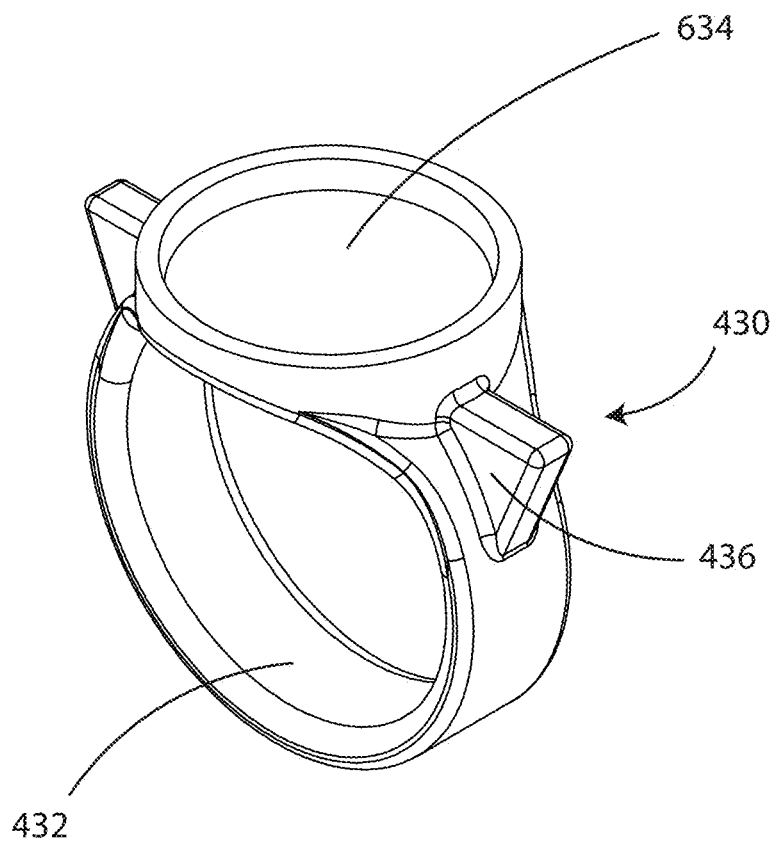
FIG. 18 is a perspective view of an embodiment of a peritoneal dialysis cap base element.
Figure 19:
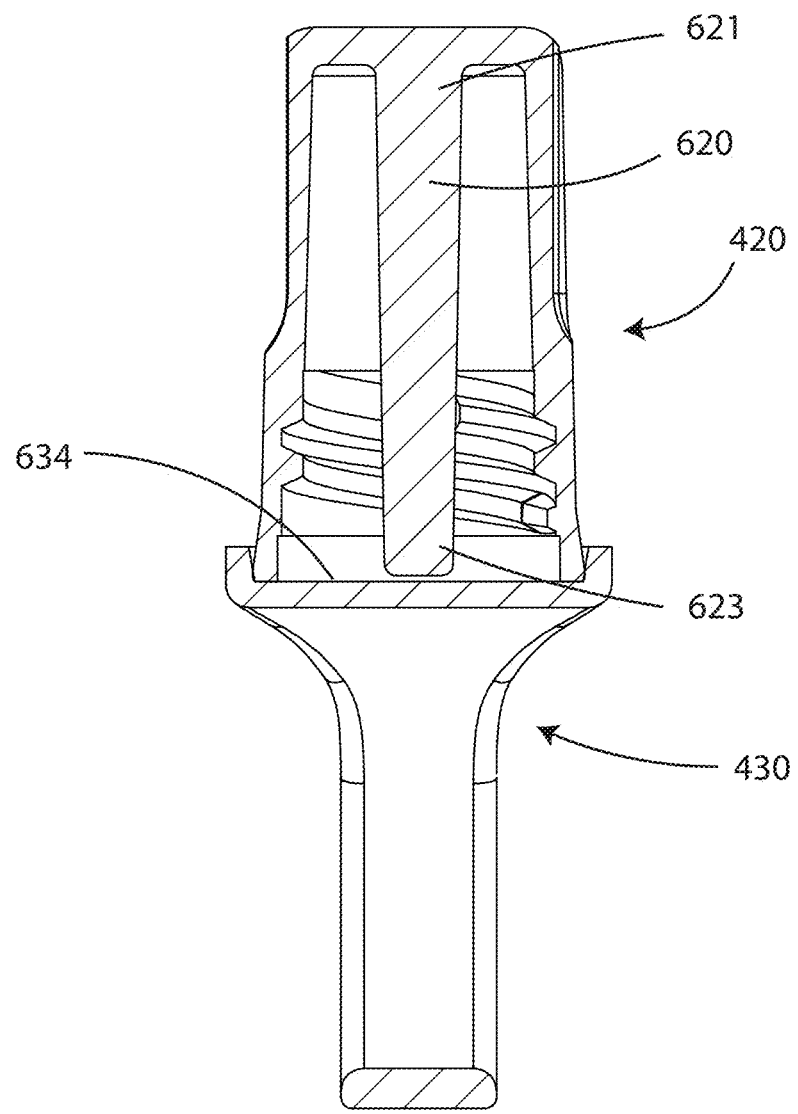
FIG. 19 is a cross-sectional view of an embodiment of a peritoneal dialysis cap and base element.

FIG. 18 is a perspective view of an embodiment of a peritoneal dialysis base element 430, having a ring 432, side extensions 436, and a recess 634. FIG. 19 is a cross-sectional view of an embodiment of a peritoneal dialysis cap 420 and the embodiment of the base element 430 shown in FIG. 18 through a longitudinally axial centerline of the base element 430. In any embodiments of the base element disclosed herein (including, without limitation, base element 430 shown in any of the FIGS. 11-12 and 18-20), the base element can have any of the features, components, materials, or other details of any other embodiments of base elements disclosed herein, in place of or in combination with any of the features, components, materials, or other details of the embodiment of the base element (including, without limitation, base element 430). In some embodiments, the distal end of the cap 420 and/or the elongate member 620 can extend into the recess 634 of the base element 430.

Figure 20:
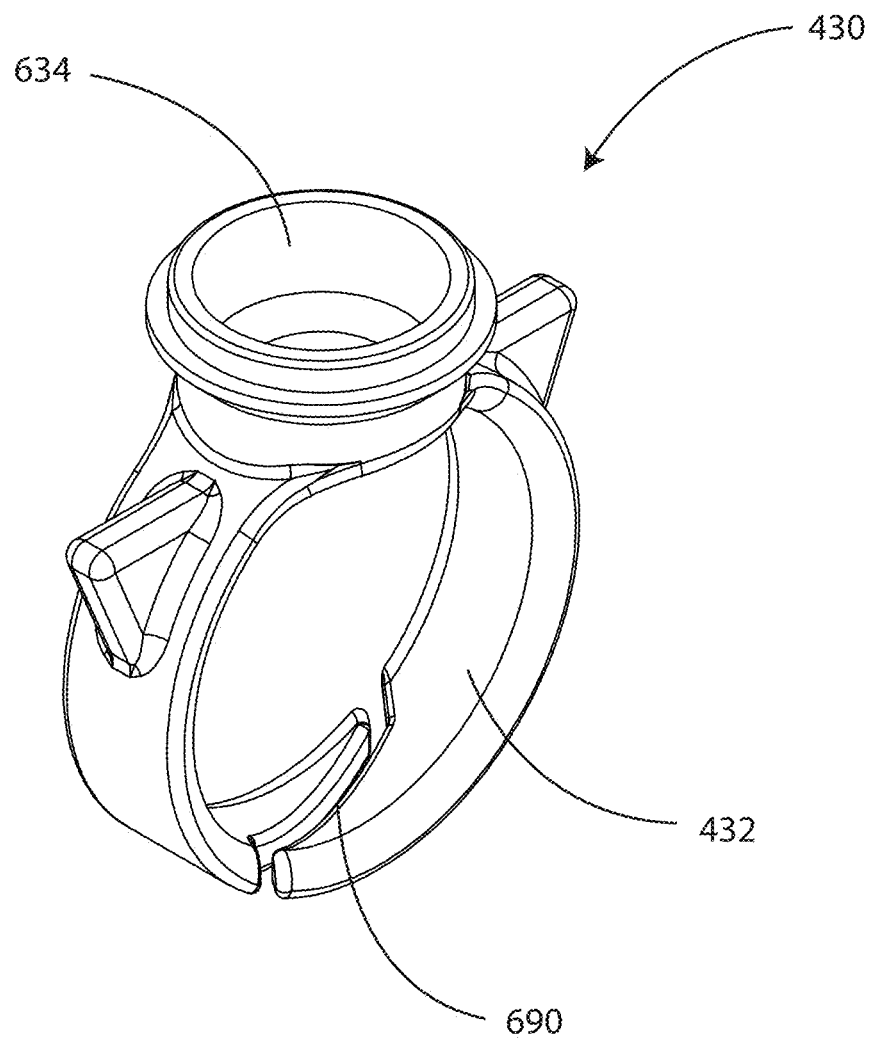
FIG. 20 is a perspective view of another embodiment of a peritoneal dialysis cap base element.

FIG. 20 is a perspective view of another embodiment of a peritoneal dialysis base element 430, showing the ring 432 with a split region 690 in the ring 432. In some embodiments, the split region 690 in the ring 432 can allow the ring to expand (e.g., increase) and contract (e.g., decrease) in size to accommodate different sized fingers of users.

Figure 21:
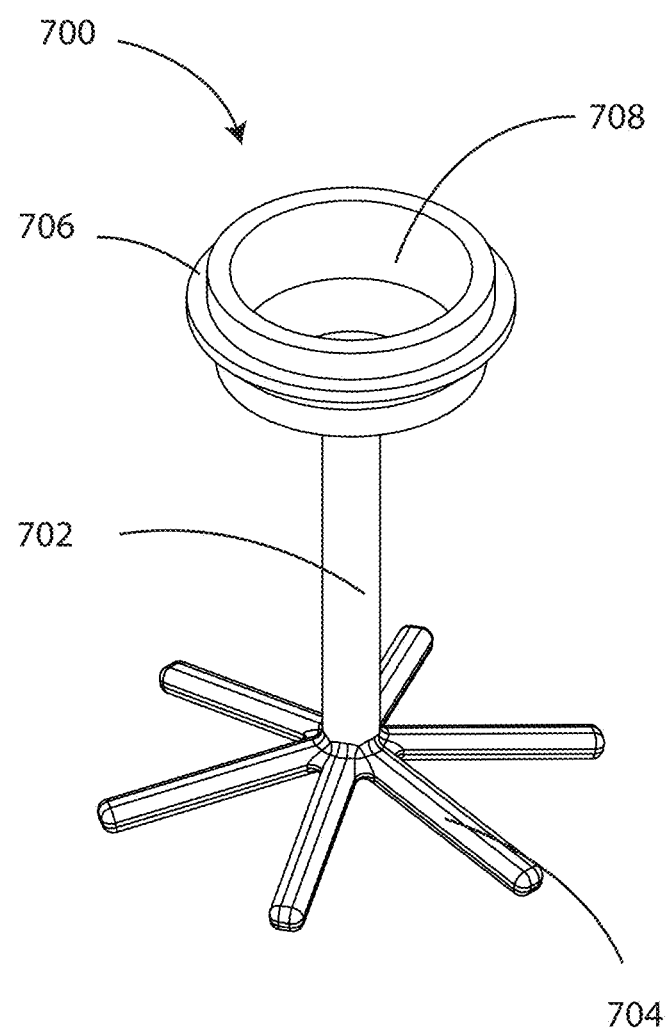
FIG. 21 is a perspective view of another embodiment of a peritoneal dialysis cap base element.

FIG. 21 is a perspective view of another embodiment of a peritoneal dialysis base element 700. In any embodiments of the base element disclosed herein (including, without limitation, the embodiment of the base element 700 shown in FIG. 21), the base element can have any of the features, components, materials, or other details of any other base element embodiments disclosed herein, in place of or in combination with any of the features, components, materials, or other details of the embodiment of the base element (including, without limitation, base element 700). With reference to FIG. 21, some embodiments of the base element 700 can have a shaft 702 and a multi-prong retaining region 704 that can be grasped by the user. The base element 700 can have an annular flange or ledge 706 that is sized and configured to receive the distal end portion of the cap, and a recess 708 formed in an end of the base element 700 into which the distal end of an elongate member of the cap can extend.

Figure 22:
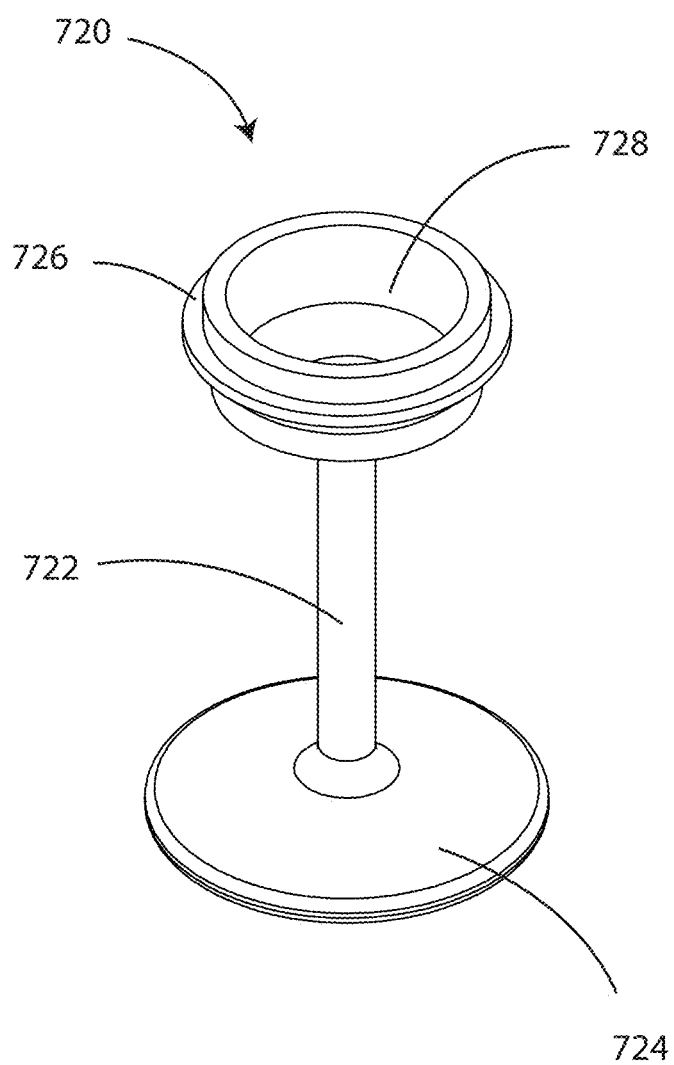
FIG. 22 is a perspective view of another embodiment of a peritoneal dialysis cap base element.

FIG. 22 is a perspective view of another embodiment of a peritoneal dialysis base element 720. In any embodiments of the base element disclosed herein (including, without limitation, the embodiment of the base element 720 shown in FIG. 22), the base element can have any of the features, components, materials, or other details of any other base element embodiments disclosed herein, in place of or in combination with any of the features, components, materials, or other details of the embodiment of the base element (including, without limitation, base element 720). With reference to FIG. 22, some embodiments of the base element 720 can have a shaft 722 and a circular or disk shaped retaining region 724 that can be grasped by the user. The base element 720 can have an annular flange or ledge 726 that is sized and configured to receive the distal end portion of the cap, and a recess 728 formed in an end of the base element 720 into which the distal end of an elongate member of the cap can extend.

Figure 23:
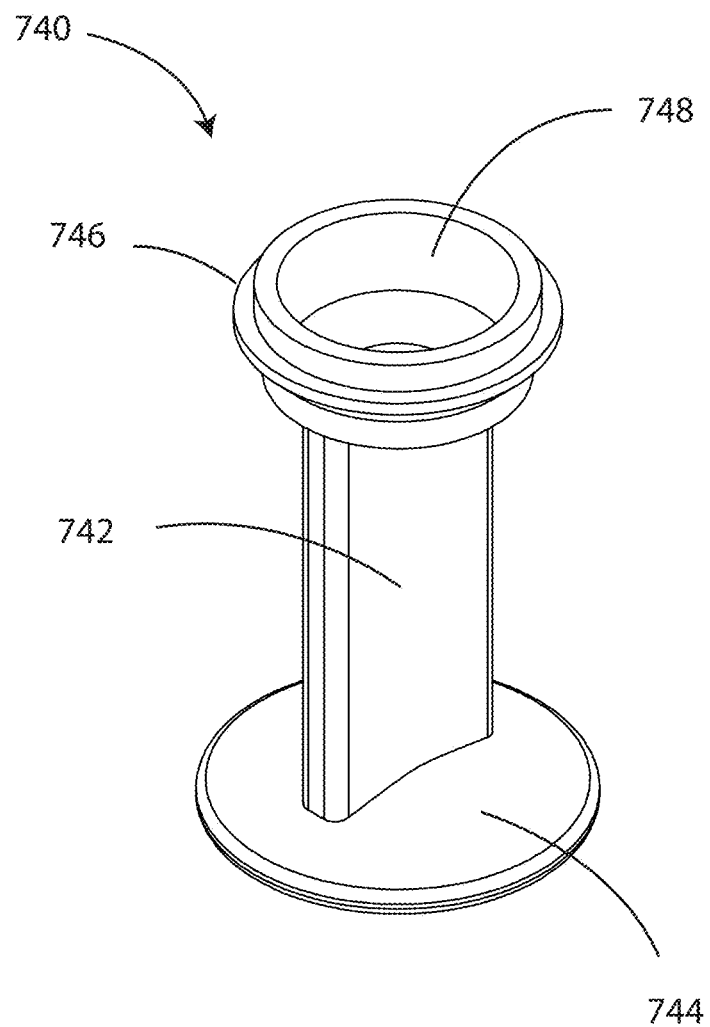
FIG. 23 is a perspective view of another embodiment of a peritoneal dialysis cap base element made in accordance with various embodiments herein.

FIG. 23 is a perspective view of another embodiment of a peritoneal dialysis base element 740. In any embodiments of the base element disclosed herein (including, without limitation, the embodiment of the base element 740 shown in FIG. 23), the base element can have any of the features, components, materials, or other details of any other base element embodiments disclosed herein, in place of or in combination with any of the features, components, materials, or other details of the embodiment of the base element (including, without limitation, base element 740). With reference to FIG. 23, some embodiments of the base element 740 can have a shaft 742 and a circular or disk shaped retaining region 744 that can be grasped by the user. The shaft 742 can have a generally rectangular shaped cross-section. The base element 740 can have an annular flange or ledge 746 that is sized and configured to receive the distal end portion of the cap, and a recess 748 formed in an end of the base element 740 into which the distal end of an elongate member of the cap can extend.

In any embodiments disclosed herein, the cap can include an antimicrobial agent, for example and without limitation, chlorhexidine acetate. Other antimicrobial agents that can be used with any embodiments disclosed herein can include chlorhexidine base, chlorhexidine acetate, chlorhexidine gluconate, EDTA, silver sulfadiazine, or Taurolidine, or combinations thereof. Other suitable antimicrobial agents can also be used with any cap embodiments disclosed herein. The term "antimicrobial," as used here, can include any substance or substances that kills or inhibits the growth of organisms such as bacteria, fungi, protozoa, viruses, etc. It should also be noted that there can be one or more antimicrobial agents used in some embodiments disclosed herein. Therefore, throughout this document, the term antimicrobial or antimicrobial agent should be understood to refer to one or more antimicrobial agents.

In any embodiments disclosed herein, the antimicrobial agent can be coated on the elongate member and/or on other surfaces of the cap, such as an inside surface of the body of the cap, and/or a proximal wall of the cap. As such, the antimicrobial agent can be delivered as a coating that elutes from a coated elongate member, that is coated on, or impregnated into, an elongate member (such as 250 µg or approximately 250 µg of chlorhexidine acetate in a layer 2 µm or approximately 2 µm thick along a length of the elongate member, or as 50 µg or approximately 50 µg of chlorhexidine acetate in a layer that is 0.4 µm thick or approximately 0.4 µm thick). Antimicrobial agent from the cap can dissolve into the displaced fluid, thereby disinfecting the proximal end of the catheter. In this arrangement, the antimicrobial can be transferred from the cap to the solution within the catheter. The antimicrobial substance or agent from the cap can dissolve into the catheter fluid, thereby disinfecting at least the proximal end of the catheter. Furthermore, in some embodiments, when the catheter fluid dries, the catheter fluid can leave deposits or coatings of chlorhexidine acetate or other appropriate antimicrobial on the cap and/or catheter hub.

In some embodiments, the elongate member can be configured to displace a volume of fluid from within the catheter as the elongate member is advanced into the hub of the catheter. In some embodiments, the volume of fluid that can be displaced can equal or approximately the volume of the coated or uncoated elongate member. In some embodiments, the volume of fluid that can be displaced can equal or approximately equal the volume of the coated or uncoated elongate member that extends past the porous element in the distal direction, or the volume of the coated or uncoated elongate member minus the solid or displacement volume of the porous element.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. The ranges disclosed herein also encompass any and all overlap, sub-ranges, and combinations thereof, and any specific values within those ranges. Language such as "up to," "at least," "greater than," "less than," "between," and the like includes the number recited. Numbers and values used herein preceded by a term such as "about" or "approximately" include the recited numbers. For example, "approximately 7 mm" includes "7 mm" and numbers and ranges preceded by a term such as "about" or "approximately" should be interpreted as disclosing numbers and ranges with or without such a term in front of the number or value such that this application supports claiming the numbers, values and ranges disclosed in the specification and/or claims with or without the term such as "about" or "approximately" before such numbers, values or ranges such, for example, that "approximately two times to approximately five times" also includes the disclosure of the range of "two times to five times." The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

The following is claimed:

1. A cap for a medical connector, the cap comprising:
   a body having a closed proximal end and an open distal end;
   an interior volume within the body;
   an elongate member extending from the proximal end of the body axially through at least a portion of the interior volume, the elongate member comprising a dry antimicrobial on a surface thereof;
   threads for securing the cap to a medical connector;
   a porous element in the interior volume within the body, wherein the porous element is not saturated with an antimicrobial before use; and
   a radially inwardly facing sealing surface on the cap, the inwardly facing sealing surface located distal to the threads and providing a liquid-tight seal between the cap and the medical connector when the cap is installed on the medical connector.

2. The cap for a medical connector of claim 1, wherein the radially inwardly facing sealing surface on the cap provides a liquid-tight seal between the cap and the medical connector when the cap is installed on the medical connector by constricting around an outer surface of the medical connector.

3. The cap for a medical connector of claim 1, further comprising a distally facing sealing surface on the cap, wherein:
   the distally facing sealing surface is located distal to the threads; and
   the distally facing sealing surface provides a second liquid-tight seal between the cap and the medical connector when the cap is installed on the medical connector.

4. The cap for a medical connector of claim 1, wherein all sealing surfaces are located in a distal portion of the body of the cap.

5. The cap for a medical connector of claim 1, wherein the porous element encloses a volume from 75 to 125 percent of a volume of liquid that can be displaced by the elongate member as the elongate member is advanced into the medical connector.

6. The cap for a medical connector of claim 1, wherein the porous element is sized and configured to contact an end of the medical connector when the cap is engaged with the medical connector.

7. The cap for a medical connector of claim 1, wherein the elongate member does not form a fluid seal within a lumen of the medical connector.

8. The cap for a medical connector of claim 1, wherein the antimicrobial comprises chlorhexidine acetate.

9. A kit comprising the cap for a medical connector of claim 1 and a base element, wherein the cap is coupled with the base element.

10. The cap for a medical connector of claim 1, wherein the porous element is substantially free of an antimicrobial before use.

11. The cap for a medical connector of claim 1, wherein the porous element is at least 95% free of an antimicrobial before use.

12. The cap for a medical connector of claim 1, wherein the medical connector is part of a peritoneal dialysis transfer set.

13. The cap for a medical connector of claim 1, wherein the cap is configured to overlap a portion of an outer surface of the medical connector and to create a seal against the portion of the outer surface of the medical connector that is overlapped.

14. The cap for a medical connector of claim 1, wherein the porous element is configured to retain a fluid exiting the medical connector upon installation of the cap on a transfer set.

15. The cap for a medical connector of claim 3, wherein the distally facing sealing surface is located at a distal end of the cap and has a generally planar surface that is approximately perpendicular to a longitudinally axial centerline of the cap.

16. A cap for a medical connector, the cap comprising:
a body having a closed proximal end and an open distal end;
an interior volume within the body;
an elongate member extending from the proximal end of the body axially through at least a portion of the interior volume, the elongate member comprising a dry antimicrobial on a surface thereof;
threads for securing the cap to a medical connector;
a porous element in the interior volume within the body, wherein the porous element is not saturated with an antimicrobial before use; and
a radially inwardly facing sealing surface on the cap, the inwardly facing sealing surface located distal to the threads and providing a liquid-tight seal between the cap and the medical connector when the cap is installed on the medical connector;
wherein the porous element is substantially free of an antimicrobial before use.

17. The cap for a medical connector of claim 16, further comprising a distally facing sealing surface on the cap, wherein:
the distally facing sealing surface is located distal to the threads; and
the distally facing sealing surface provides a second liquid-tight seal between the cap and the medical connector when the cap is installed on the medical connector.

18. The cap for a medical connector of claim 16, wherein the antimicrobial comprises chlorhexidine acetate.

19. A kit comprising the cap for a medical connector of claim 16 and a base element, wherein the cap is coupled with the base element.

20. The cap for a medical connector of claim 17, wherein the distally facing sealing surface is located at a distal end of the cap and has a generally planar surface that is approximately perpendicular to a longitudinally axial centerline of the cap.

21. A cap for a medical connector, the cap comprising:
a body having a closed proximal end and an open distal end;
an interior volume within the body;
an elongate member extending from the proximal end of the body axially through at least a portion of the interior volume, the elongate member comprising a dry antimicrobial on a surface thereof;
threads for securing the cap to a medical connector;
a porous element in the interior volume within the body, wherein the porous element is not saturated with an antimicrobial before use; and
a radially inwardly facing sealing surface on the cap, the inwardly facing sealing surface located distal to the threads and providing a liquid-tight seal between the cap and the medical connector when the cap is installed on the medical connector;
wherein the porous element is sized and configured to contact an end of the medical connector when the cap is engaged with the medical connector.

22. The cap for a medical connector of claim 21, further comprising a distally facing sealing surface on the cap, wherein:
the distally facing sealing surface is located distal to the threads; and
the distally facing sealing surface provides a second liquid-tight seal between the cap and the medical connector when the cap is installed on the medical connector.

23. The cap for a medical connector of claim 21, wherein the antimicrobial comprises chlorhexidine acetate.

24. A kit comprising the cap for a medical connector of claim 21 and a base element, wherein the cap is coupled with the base element.

25. The cap for a medical connector of claim 22, wherein the distally facing sealing surface is located at a distal end of the cap and has a generally planar surface that is approximately perpendicular to a longitudinally axial centerline of the cap.

* * * * *